United States Patent
Xia et al.

(10) Patent No.: US 10,988,774 B2
(45) Date of Patent: Apr. 27, 2021

(54) SYSTEM FOR SITE-SPECIFIC MODIFICATION OF ALS GENE USING CRISPR-CAS9 SYSTEM FOR PRODUCTION OF HERBICIDE-RESISTANT RICE AND USE OF SAME

(71) Applicant: Institute of Crop Sciences, Chinese Academy of Agricultural Sciences, Beijing (CN)

(72) Inventors: LanQin Xia, Beijing (CN); YongWei Sun, Beijing (CN); YunDe Zhao, Beijing (CN); YouZhi Ma, Beijing (CN); ChuanYin Wu, Beijing (CN); Xin Zhang, Beijing (CN)

(73) Assignee: INSTITUTE OF CROP SCIENCES, CHINESE ACADEMY OF AGRICULTURAL SCIENCES, Beijing (CN)

( * ) Notice: Subject to any disclaimer, the term of this patent is extended or adjusted under 35 U.S.C. 154(b) by 160 days.

(21) Appl. No.: 15/779,825

(22) PCT Filed: Mar. 25, 2016

(86) PCT No.: PCT/CN2016/077337
§ 371 (c)(1),
(2) Date: May 29, 2018

(87) PCT Pub. No.: WO2017/092201
PCT Pub. Date: Jun. 8, 2017

(65) Prior Publication Data
US 2019/0085356 A1    Mar. 21, 2019

(30) Foreign Application Priority Data
Nov. 30, 2015 (CN) .......................... 201510854747.8

(51) Int. Cl.
*C12N 15/82* (2006.01)
*C12N 15/62* (2006.01)

(52) U.S. Cl.
CPC ......... *C12N 15/8278* (2013.01); *C12N 15/62* (2013.01); *C12N 15/8213* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2015/0059010 A1* | 2/2015 | Cigan | C12N 15/8216 800/260 |
| 2015/0067922 A1* | 3/2015 | Yang | C12N 15/8245 800/298 |
| 2015/0211058 A1 | 7/2015 | Carstens | |
| 2018/0230476 A1* | 8/2018 | Cigan | C12N 15/8201 |

FOREIGN PATENT DOCUMENTS

| | | |
|---|---|---|
| CN | 105002214 A | 10/2015 |
| WO | WO 2014/065596 A1 * | 5/2014 |
| WO | 2015026886 A1 | 2/2015 |
| WO | WO2015/026886 A1 * | 2/2015 |

OTHER PUBLICATIONS

Endo et al. (2013) Food Nutr Sci 4:522-28.*
Endo et al. (2007) Plant J 52:157-66.*
Guo et al. (2004) Proc Natl Acad Sci USA 101:9205-10.*
Miao et al. (2013) Cell Res 23:1233-36.*
Merriam-Webster "Target" accessed Aug. 15, 2020.*
Swanson, E. et al., "Microspore mutagenesis and selection: Canola plants with field tolerance to the imidazolinones," Theoretical and Applied Genetics, vol. 78, No. 4, Oct. 1989, 6 pages.
Endo, M. et al., "Molecular breeding of a novel herbicide-tolerant rice by gene targeting," The Plant Journal, vol. 52, No. 1, Oct. 2007, 10 pages.
Shan, Q. et al., "Targeted genome modification of crop plants using a CRISOR-Cas system," Nature Biotechnology, vol. 31, No. 8, Aug. 2013, 3 pages.
Miao, J. et al., "Targeted mutagenesis in rice using CRISPR-Cas system," Cell Research, vol. 23, No. 10, Oct. 2013, Published Online Sep. 3, 2013, 4 pages.
Zhang, H. et al., "The CRISPR/Cas9 system produces specific and homozygous targeted gene editing in rice in one generation," Plant Biotechnology Journal, vol. 12, No. 6, Aug. 2014, Published Online May 23, 2014, 11 pages.
Wang, Y. et al., "Simultaneous editing of three homoeoalleles in hexaploid bread wheat confers heritable resistance to powdery mildew," Nature Biotechnology, vol. 32, No. 9, Sep. 2014, Published Online Jul. 20, 2014, 6 pages.

(Continued)

*Primary Examiner* — Russell T Boggs
(74) *Attorney, Agent, or Firm* — McCoy Russell LLP

(57) ABSTRACT

The present invention discloses a system for site-specific modification of ALS gene by a CRISPR-Cas9 system to produce herbicide-resistant rice, and uses thereof. The system for site-specific modification in a plant genome of the present invention comprises a vector for site-specific modification in a plant genome and a donor DNA; wherein the vector for site-specific modification in a plant genome comprises a Cas9 protein expression cassette, gRNA expression cassettes and a donor DNA; the gRNA expression cassettes encode two gRNAs targeting two target sites of a target DNA of a plant of interest, respectively; the target DNA has a fragment to be site-specifically modified which is positioned between the two target site.

14 Claims, 2 Drawing Sheets
(2 of 2 Drawing Sheet(s) Filed in Color)
Specification includes a Sequence Listing.

(56) References Cited

OTHER PUBLICATIONS

Schiml, S. et al., "The CRISPR/Cas system can be used as nuclease for in planta gene targeting and as paired nickases for directed mutagenesis in Arabidopsis resulting in heritable progeny," The Plant Journal, vol. 80, No. 6, Dec. 2014, Published Online Oct. 18, 2014, 12 pages.

"Cibus SU Canola," Cibus Website, Available Online at https://www.cibus.com/products.php, Available as Early as Apr. 9, 2015, 4 pages.

Ma, X. et al., "A Robust CRISPR/CAS9 System for Convenient, High-Efficiency Multiplex Genome Editing in Monocot and Dicot Plants," Molecular Plant, vol. 8, No. 8, Aug. 2015, Published Online Apr. 24, 2015, 11 pages.

Svitashev, S. et al., "Targeted Mutagenesis, Precise Gene Editing, and Site-Specific Gene Insertion in Maize Using Cas9 and Guide RNA," Plant Physiology, vol. 169, No. 2, Oct. 2015, Published Online Aug. 12, 2015, 15 pages.

Li, Z. et al., "Cas9-Guide RNA Directed Genome Editing in Soybean," Plant Physiology, vol. 169, No. 2, Oct. 2015, Published Online Aug. 20, 2015, 11 pages.

ISA State Intellectual Property Office of the People's Republic of China, International Search Report Issued in Application No. PCT/CN2016/077337, dated Sep. 2, 2016, WIPO, 4 pages.

\* cited by examiner

SYSTEM FOR SITE-SPECIFIC MODIFICATION OF ALS GENE USING CRISPR-CAS9 SYSTEM FOR PRODUCTION OF HERBICIDE-RESISTANT RICE AND USE OF SAME

CROSS-REFERENCE TO RELATED APPLICATIONS

The present application is a U.S. National Phase of International Patent Application Serial No. PCT/CN2016/077337, entitled "SYSTEM FOR OBTAINING HERBICIDE-TOLERANT RICE BY SITE-DIRECTED MODIFYING ALS GENE USING CRISPR-CAS9 SYSTEM AND USE THEREOF," filed on Mar. 25, 2016. International Patent Application Serial No. PCT/CN2016/077337 claims priority to Chinese Patent Application No. 201510854747.8, filed on Nov. 30, 2015. The entire contents of each of the above-cited applications are hereby incorporated by reference in their entirety for all purposes.

SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is Substitute Sequence_Listing_JEE17318PCTUS.txt, the date of creation of the ASCII text file is Nov. 27, 2018, and the size of the ASCII text file is 44.21 KB. The material in this submitted text file is hereby incorporated by reference in its entirety into this application.

TECHNICAL FIELD

The present invention belongs to the field of gene engineering, and specifically, relates to a system for site-specific modification of ALS gene using a CRISPR-Cas9 system (CRISPR/Cas9 system) to obtain herbicide-resistant rice, and use thereof.

BACKGROUND

The CRISPR/Cas9 system is a new technology for genome site-specific editing developed after technologies such as ZFNs and TALENs. Unlike ZFNs and TALENs, the CRISPR/Cas9 system identifies a target site depending on complementary base pairing between bases of the nucleic acids, enables editing of any of 20 bp target sequence immediately following PAM (NGG) with a high distribution frequency in a genome, and thus can more easily find a suitable target for a target gene to be site-specifically edited. Further, the CRISPR/Cas9 system allows for concurrent directed-editing at different sites of the same gene or at sites of various genes, leading to more flexible application thereof. Furthermore, the CRISPR/Cas9 system can be simply and quickly operated in such a way that only a 20-30 bp nucleotide sequence of the initial vector needs to be replaced for each targeting, and therefore is more suitable for large-scale and high-throughput operation. CRISPR/Cas9, as a new technology for modifying a target gene, exhibits a broad development potential and application prospect, and is promising to be one of the most powerful tools for gene directed editing in the future. To date, the CRISPR/Cas9 has been applied for studies on site-specific knockout in genomes of rice, wheat, Arabidopsis as well as Nicotiana benthamiana, however, there are not yet studies on site-specific modification (amino acid replacement or site-specific integration) in important crops for genetic improvement of agronomic traits of interest.

The uses of the CRISRP/Cas9 system for editing the genome of crops are mainly divided into three types, gene site-specific knockout process for obtaining mutants, site-specific modification for target gene, and site-specific integration of exogenous gene. Among these, site-specific knockout is reported the most in the art, due to its characteristics such as easy operation, mature technology. Shan et al., (2013), has successfully produced rice gene mutants OsBADH2 and OsPDS, at a mutation rate of 7.1%-9.4% (Shan et al. Targeted genome modification of crop plant using a CRISPR-Cas system: Nat Biotechnol. 2013 August; 31(8):686-8.). Wang et al., (2013), has performed successful site-specific knockout of wheat gene TaMLO-A1 by CRISPR technology (Wang et al., Simultaneous editing of three homoeoalleles in hexaploid bread wheat confers heritable resistance to powdery mildew: Nat Biotechnol. 2014 September;32(9):947-51. doi: 10.1038/nbt.2969). Miao et al. (2013), conducted editing of rice chlorophyll synthesis gene CAO1 and tiller angle regulating gene LAZY, and as a result, 83.3% of T0 generation of transgenic plants had a mutation at the corresponding site of CAO1 gene, and up to 91.6% of transgenic plants had a mutation at the corresponding site of LAZY gene, wherein homozygous mutants of LAZY gene were included in a ratio of up to 50%, all of which exhibited a phenotype with larger tiller angle (Miao et al., Targeted mutagenesis in rice using CRISPR-Cas system: Cell Res. 2013 October; 23(10): 1233-1236). Zhang et al., (2014), analyzed the efficiency, characteristics, heritability, specificity, etc. of the CRISPR/Cas9-induced mutations in 11 target genes from two rice subspecies (Japonica rice, Nipponbare; and Indica rice, Kasalath), and found that the mutation efficiency was up to 66.7% in T0 generation transgenic plants, and homozygous mutants were obtained for the target gene site in more than half of T0 generation, with the genetic transmission of mutant progenies being followed the classic Mendelian law (Zhang et al., The CRISPR/Cas9 system produces specific and homozygous targeted gene editing in rice in one generation: Plant Biotechnol J. 2014 August;12(6):797-807. doi: 10.1111/pbi.12200). Ma et al. (2015), performed editing at a total of 46 target sites in rice using the CRISPR/Cas9 system, enabling mutations at a mean rate of 85.4%, most of which were uniform biallelic mutation (54.9%) and homozygous mutation (24.7%), and were inheritable to progenies. The above studies indicate that site-specific mutation of specific genes in crops can be efficiently achieved by using the CRISPR/Cas9 system (Ma et al., A Robust CRISPR/Cas9 System for Convenient, High-Efficiency Multiplex Genome Editing in Monocot and Dicot Plants: Mol Plant. 2015 August;8(8):1274-84. doi: 10.1016/j.molp.2015.04.007).

There are only a few reports of the studies on site-specific amino acid replacement and exogenous gene site-specific integration in plants using a CRISRP/Cas9 system. In Miao et al,.(2013), GUS activity was detected by introducing a GUUS gene and a CRISPR/Cas9 system into rice, suggesting the occurrence of homologous recombination. Schiml et al., (2014), constructed CRISPR/Cas9 and a template DNA having the same sequence as a spacer at both ends thereof into the same T-DNA to transform Arabidopsis thaliana, and inserted accurately a kanamycin-resistant gene nptII at a target site of AtADH1 gene through homology-directed repair pathway (Schiml et al., The CRISPR/Cas system can be used as nuclease for in planta gene targeting and as paired nickases for directed mutagenesis in Arabidopsis resulting in heritable progeny: Plant J. 2014 December;80(6):1139-50. doi: 10.1111/tpj.12704). Li et al., (2015), introduced both an exogenous fragment and CRISPR/Cas9 into a soybean, and detected a successfully site-specifically modified ALS1 gene in calli, but no plant was obtained yet. However, when both an anti-hygromycin gene expression cassette and a CRISPR/Cas9 system were simultaneously introduced into a soybean, homologous recombination lines were identified and confirmed by PCR and Southern blot, with inheritance of the integrated gene being consistent with Mendelian law (Li et al., Cas9-Guide RNA Directed Genome Editing in Soybean, Plant Physiology August 2015, pp.00783.2015; DOI: 10.1104/pp.15.00783). Svitashev et al., (2015), site-specifically recombined liguleless-1 gene into a corn genome through homologous recombination. Moreover, when both a CRISPR/Cas9 system and an exogenous modifying fragment (double- or single- stranded DNA) were simultaneously introduced into corn through a biolistic or Agrobacterium-mediated method, proline at position 165 of ALS2 in the plant was successfully modified to serine (P165S) and the resistance to sulfonylurea-based herbicide was obtained (Svitashev et al., Targeted Mutagenesis, Precise Gene Editing, and Site-Specific Gene Insertion in Maize Using Cas9 and Guide RNA Plant Physiology August 2015, pp.00793.2015; DOI: 10.1104/pp.15.00793).

Through genome editing-mediated homologous recombination, site-specific modification enables improvement of herbicide resistance of important crops, which is one of focuses in the current studies of genome editing. Traditional methods for producing herbicide-resistant crops mainly include: (1) improving herbicide resistance of crops by introduction of exogenous genes (epsps, bar, pmi, etc.), which has been widely reported, but has a limitation in widespread application in important food crops, because the resultant crops belong to transgenic crops so that there is no commercial production of herbicide-resistant transgenic wheat and rice reported yet; in addition, it is concerned with safety issues of transgenic organisms such as formation of super weeds due to herbicide-resistant genetic drift; (2) improving the herbicide resistance of important crops by mutagenesis of endogenous genes in the crops through the use of ethyl methanesulfonate (EMS), as the key enzymes in amino acid synthesis of a plant are always significant target enzymes in the development of new herbicides, which has been reported for use in wheat, barley, rice, and the like, but is very difficult for widespread use due to randomness of EMS mutagenesis that necessitates large-scale and extensive screening for mutants with herbicide resistance but unchanged other agronomic traits.

Target acetolactate synthase (ALS) inhibitor type herbicide, Bispyribac-sodium, is currently the largest interest in the development. Acetolactate synthase (ALS) is present in plants, which can play a catalytic role in conversion from pyruvate to acetolactate with high specificity and very high catalytic efficacy, thereby synthesize 3 essential branched amino acids (valine, leucine and isoleucine) in plants. Sulfonylurea-based, imidazolidinone-based, pyrimidine carboxylate-based herbicides can inhibit ALS activity, destroy the synthesis of valine, leucine and isoleucin in plants, thereby resulting in death of the plants. Swanson et al. (1989) produced 2 rape mutants, PM1 and PM2, which were resistant to imidazolidinone herbicides, by a method of microspore chemical mutagenesis, wherein both of PM1 and PM2 were produced from point mutation in ALS gene, PM1 being a gene BnALS1 with serine at position 653 mutated, and PM2 being a gene BnALS2 with tryptophan at position 574 mutated (numbered from the position of the amino acid of ALS of Arabidopsis thaliana). Cibus Global company successfully produced an ALS gene-edited sulfonylurea-based herbicides resistant rape plant by single-nucleotide gene repair technique (Gene Repair OligoNucleotide technology) in March 2014, which has been commercially produced by far in Canada. Sulfonylurea-based, imidazolidinone-based, and pyrimidine carboxylate-based herbicides have been broadly applied in production, which have the advantages of high bioactivity and broad weeding, as well as safety to human and animals (Endo et al.,2007).

DISCLOSURE OF INVENTION

The present invention provides a system for site-specific modification of ALS gene using a CRISPR-Cas9 system to produce herbicide-resistant rice, and applications thereof.

The system for site-specific modification in a plant genome provided by the present invention comprises a vector for site-specific modification in a plant genome, and a donor DNA A, wherein the vector comprises a Cas9 protein expression cassette, gRNA expression cassettes, and a donor DNA B; wherein the gRNA expression cassettes encode two gRNAs targeting two target sites in a target DNA of a plant of interest, respectively; the target DNA has a fragment to be site-specifically modified which is positioned between the two target site; of the two target sites, the target site positioned upstream is called upstream target site, and the target site positioned downstream called downstream target site.

The donor DNA B contains the upstream target site, the downstream target site, and a fragment for site-specific modification between the upstream target site and the downstream target site; the fragment for site-specific modification is a DNA fragment to replace the fragment to be site-specifically modified.

The donor DNA A has the same nucleotide sequence as that of the donor DNA B.

The Cas9 protein expression cassette, the gRNA expression cassettes, and the donor DNA B can be present in the same plasmid, in two plasmids in any combinations thereof, or in respective plasmids.

In the system described above, the site-specific modification may be amino acid replacement, exogenous gene site-specific integration, or exogenous fragment site-specific integration.

In the system described above, the donor DNA B may further contain a upstream homologous arm and a downstream homologous arm for homologous recombination with the target DNA, with the upstream homologous arm positioned between the upstream target site and the fragment for site-specific modification, and the downstream homologous arm positioned between the fragment for site-specific modification and the downstream target site.

In the system described above, the plant or the plant of interest may be a monocotyledonous or dicotyledonous plant. The monocotyledonous plant may be a gramineous plant. Further, the gramineous plant may be particularly rice, e.g., Nipponbare rice.

In the system described above, the target DNA may be a gene encoding acetolactate synthase; the acetolactate synthase may be a1 or a2:

a1, a protein having an amino acid sequence as represented by SEQ ID NO: 2 in the sequence listing;

a2, a protein derived from a1, having the activity of acetolactate synthase, with replacement and/or deletion and/or addition of one or several amino acid residues in SEQ ID NO: 2.

The target DNA has a nucleotide sequence particularly as represented by SEQ ID NO: 3 in the sequence listing.

The upstream target site may be particularly represented by the nucleotides at positions 7590-7609 from 5'-end of SEQ ID NO: 1 in the sequence listing. The downstream target site may be particularly represented by the nucleotides at positions 8032-8051 from 5'-end of SEQ ID NO: 1 in the sequence listing. The fragment for site-specific modification may be particularly represented by the nucleotides at positions 7716-7979 from 5'-end of SEQ ID NO: 1 in the sequence listing.

The gRNA expression cassettes include a gRNA expression cassette 1 and a gRNA expression cassette 2. The gRNA expression cassette 1 encodes gRNA1 (e.g., gRNAW548L), and the gRNA expression cassette 2 encodes gRNA2 (e.g., gRNAS627I). The gRNA1 targets the upstream target site, and the gRNA2 targets the downstream target site.

The Cas9 protein expression cassette comprises a promoter to initiate the transcription of Cas9 gene (e.g., Ubiquitin promoter), a Cas9 gene, and a terminator to stop the transcription of Cas9 gene (e.g., NOS terminator). The gRNA expression cassette 1 comprises a promoter to start the transcription of a gRNA1 encoding gene (e.g., rice promoter U3), the gRNA1 encoding gene, and a terminator to stop the transcription of the gRNA1 encoding gene (e.g., Poly-A terminator). The gRNA expression cassette 2 comprises a promoter to start the transcription of a gRNA2 encoding gene (e.g., rice promoter U3), the gRNA2 encoding gene, and a terminator to stop the transcription of the gRNA2 encoding gene (e.g., Poly-T terminator).

The gRNA expression cassette 1 (e.g., gRNAW548L expression cassette) may be particularly represented by the nucleotides at positions 261-747 from 5'-end of SEQ ID NO: 1 in the sequence listing. The gRNA expression cassette 2 (e.g., gRNAS627I expression cassette) may be particularly represented by the nucleotides at positions 8328-8814 from 5'-end of SEQ ID NO: 1 in the sequence listing.

In the system described above, the vector for the site-specific modification in a plant genome may be a recombinant vector, pCXUN-cas9-gRNA548-gRNA627-arm donor, as represented by SEQ ID NO: 1 in the sequence listing. In the SEQ ID NO: 1, the nucleotides at positions 900-7570 constitute the Cas9 protein expression cassette (the nucleotides at positions 5580-7570 constitute the Ubiquitin promoter to start the transcription of Cas9 protein gene, the nucleotides at positions 1446-5576 constitute the Cas9 protein gene, and the nucleotides at positions 900-1152 constitute the NOS terminator to stop the transcription of Cas9 protein gene), nucleotides at positions 261-747 constitute the gRNA expression cassette 1 (the nucleotides at positions 367-747 constitute the rice promoter U3 to start the transcription of gRNA1 encoding gene, the nucleotides at positions 271-366 constitute the gRNA1 encoding gene, and the nucleotides at positions 261-270 constitute the Poly-A terminator to stop the gRNA1 encoding gene transcription), the nucleotides at positions 8328-8814 constitute the gRNA expression cassette 2 (the nucleotides at positions 8328-8708 constitute the rice promoter U3 to start the gRNA2 encoding gene transcription, the nucleotides at positions 8709-8804 constitute the gRNA2 encoding gene, and the nucleotides at positions 8805-8814 constitute the Poly-T terminator to stop the gRNA2 encoding gene transcription), and the nucleotides at positions 7590-8051 constitute the donor DNA B (the nucleotides at positions 7590-7609 constitute the upstream target site, the nucleotides at positions 7616-7715 constitute the upstream homologous arm, the nucleotides at positions 7716-7979 constitute the fragment for site-specific modification, the nucleotides at positions 7980-8025 constitute the downstream homologous arm, and the nucleotides at positions 8032-8051 constitute the downstream target site).

In the system described above, the donor DNA A may be represented by the nucleotides at positions 7590-8051 from 5'-end of SEQ ID NO: 1 in the sequence listing.

The system described above may further comprises other agents required for PCR amplification, agents required for gel electrophoresis, a PCR instrument, an electrophoresis equipment, a gel imaging system, and a camera.

In order to solve the technical problem aforementioned, the present invention also provides a method for site-specific modification in a plant genome.

The method for site-specific modification in a plant genome provided by the present invention comprises steps of: introducing a vector for site-specific modification in a plant genome and a donor DNA A into a plant of interest, to obtain a plant with the genome thereof site-specifically modified.

In the method described above, a molar ratio of the vector for the site-specific modification in a plant genome to the donor DNA A may be 1: (0-40), and particularly 1:20.

In the method described above, the site-specific modification may be amino acid replacement, exogenous gene site-specific integration or exogenous fragment site-specific integration.

In the above, the site-specific modification may be particularly to mutate tryptophan (W) to leucine (L) at position 548, and to mutate serine (S) to isoleucine (I) at position 627, in acetolactate synthase (ALS).

The present invention also provides uses of the system for site-specific modification in a plant genome as described above, which may be any of following 1)-5):

1) application in site-specific modification in a plant genome;
2) application in cultivation of a plant with a site-specifically modified genome;
3) application in cultivation of an herbicide-resistant plant;
4) application in plant breeding; and
5) application in a transgenic plant study using a site-specifically modified ALS gene as a marker gene for screening.

In the use described above, the site-specific modification may be amino acid replacement, exogenous gene site-specific integration, or exogenous fragment site-specific integration.

In the use described above, the site-specifically modified ALS gene is a gene encoding a site-specifically modified protein of acetolactate synthase, with tryptophan (W) (which has a codon of TGG at this position in a wild-type) mutated to leucine (L) (which has a codon of TTG at this position) at position 548, serine (S) (which has a codon of AGT at this position in a wild-type) mutated to isoleucine (I) (which has a codon of ATT at this position) at position 627, and other amino acid residues unchanged in acetolactate synthase gene as represented SEQ ID NO: 2.

In the use described above, the herbicide may be pyrimidine carboxylate-based, sulfonylurea-based, or imidazolidinone-based herbicides, and particularly pyrimidine carboxylate-based herbicides. Further, the pyrimidine carboxylate-based herbicide may be particularly Bispyribac-sodium (BS).

The plant may be a monocotyledonous plant or a dicotyledonous plant. The plant of interest may be a monocotyledonous plant or a dicotyledonous plant. The monocotyledonous plant may be a gramineous plant, and the gramineous plant may be particularly rice, e.g., Nipponbare.

As experimentally confirmed, the co-transformation of rice calli with the recombinant vector pCXUN-cas9-gRNA548-gRNA627-arm donor of the present invention constructed in vitro, which contains a Cas9 protein expression cassette, gRNA expression cassettes targeting two sites, and an exogenous fragment arm donor (donor DNA) with both ends having a gRNA-recognizable target site sequence, and the exogenous fragment arm donor by means of a gene gun, enables the success of mutations from tryptophan (W) to leucine (L) at position 548 and from serine (S) to isoleucine (I) at position 627 in acetolactate synthase (ALS), allowing for site-specific modification of rice ALS gene to obtain a homologous recombined, homozygous plant, without an off-target effect, and the homologous recombined plant has the characteristics of resistance to the herbicide, Bispyribac-sodium.

DESCRIPTION OF DRAWINGS

This application contains at least one drawing executed in color. Copies of this patent or patent application publication with color drawing(s) will be provided by the Office upon request and payment of the necessary fee.

DETAILED DESCRIPTION

Figure 1:
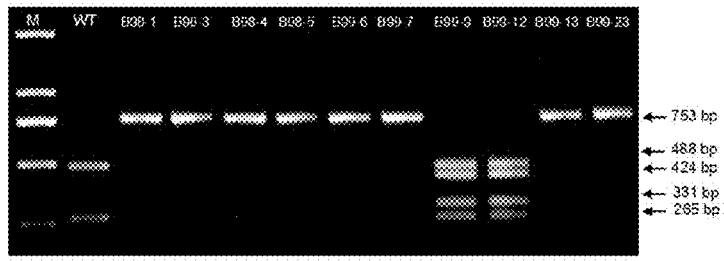
FIG. 1 shows the identification results from enzyme digestion of PCR products of part of $T_0$ generation site-specifically modified rice, wherein M is a DL2000 DNA molecular weight marker.

The present invention will be further described in details in connection with specific embodiments below, and the examples provided is intended merely to illustrate the present invention, but not to limit the scope of the present invention. The experimental methods described below in the examples are conventional methods, unless otherwise specified. The materials, reagents, etc. used in the following examples are commercially available, unless otherwise specified. The quantitative tests described in the following examples are performed in triplicate with the results averaged, unless otherwise specified.

In following examples, Nipponbare rice was used as a plant of interest for the genome site-specific modification, and the acetolactate synthase gene of Nipponbare rice served as a target DNA (as represented by SEQ ID NO: 3 in the sequence listing), to construct a site-specifically modified rice plant having tryptophan (W) (which has a codon of TGG at this position in a wild-type) mutated to leucine (L) (which has a codon of TTG at this position) at position 548, serine (S) (which has a codon of AGT at this position in a wild-type) mutated to isoleucine (I) (which has a codon of ATT at this position) at position 627 in the acetolactate synthase of Nipponbare rice.

The acetolactate synthase gene in Nipponbare rice also contains an EcoR V restriction site sequence, while the restriction site sequence has been site-specifically mutated in donor DNA (arm donor) with the amino acids thereof unchanged.

Nipponbare rice seed is a product from the National Crop Germplasm Resource Conservation Center, Institute of Crop Sciences of Chinese Academy of Agricultural Sciences. Nipponbare rice is also referred to as wild-type rice, abbreviated as WT.

Solid medium R1 (pH5.8): 4.3 g/L MS& Vitamin salts+30 g/L sucrose+0.5 g/L MES+300 mg/L casein amino acids+2.8 g/L L-proline+2 mg/L 2, 4-D+4 g/L plant gel, balanced with water.

Solid medium R4 (pH5.8): 4.3 g/L MS& Vitamin salt+30 g/L sucrose+0.5 g/L MES+2 g/L casein amino acid+30 g/L sorbitol+2 mg/L kinetin+1 mg/L NAA+4 g/L plant gel, balanced with water.

Solid medium R5 (pH5.8): 2.15 g/L MS& Vitamin salt+ 15 g/L sucrose+0.5 g/L MES+2 g/L plant gel, balanced with water.

The sequences of the primer pairs used in the following examples and purposes thereof are shown in Table 1.

TABLE 1

Sequences and Purposes of the Primer Pairs Used

| Name | Sequence | Purpose |
|---|---|---|
| 753F | SEQ ID NO: 4<br>AAGGTGAGGCAATCATCGCT | Primers for detecting |
| 753R | SEQ ID NO: 5<br>CCATGCCAAGCACATCAAAC | homologous recombination |

TABLE 1-continued

Sequences and Purposes of the Primer Pairs Used

| Name | Sequence | Purpose |
| --- | --- | --- |
| Cas9-F | SEQ ID NO: 6<br>TCGACAAGAAGTACTCCATCGGC | Detecting Cas9 |
| Cas9-R | SEQ ID NO: 7<br>CAAGAGAGAGGGCGATCAGGTTG | |
| U3F | SEQ ID NO: 8<br>GTAATTCATCCAGGTCTCCAAG | Detecting gRNA |
| U3R | SEQ ID NO: 9<br>ACGGAGAAATTTCAATGC | |
| 365F | SEQ ID NO: 10<br>GGAGAACACATGCACACTAAAAAGA | Detecting cleaved exogenous fragment |
| 365R | SEQ ID NO: 11<br>TTGGGTAACGCCAGGGTTTT | |
| OFF1F | SEQ ID NO: 12<br>GAACGCGATGCTGGAAGAAC | Off-target analysis |
| OFF1R | SEQ ID NO: 13<br>CTGTTGGCGTCGTAGAACCT | |
| OFF2F | SEQ ID NO: 14<br>GTACGAGGGGAGTAGTAGTCAGT | |
| OFF2R | SEQ ID NO: 15<br>TGAGGTTGAGCTTGTGGAGC | |
| OFF3F | SEQ ID NO: 16<br>TTTCTCCCTTGTTCGCATCTG | |
| OFF3R | SEQ ID NO: 17<br>GGCAGCTTAATCATGGGCAG | |
| OFF4F | SEQ ID NO: 18<br>AACCGCATGCTCGAGAAGAT | |
| OFF4R | SEQ ID NO: 19<br>TTGTGCACGGTACACCACTT | |
| OFF5F | SEQ ID NO: 20<br>GCACACCTGGCTCCAACC | |
| OFF5R | SEQ ID NO: 21<br>TCGGCAAACCAAGAGAACGA | |

EXAMPLE 1

Construction of Vectors for Site-Specific Mutagenesis of Acetolactate Synthase (ALS) Gene A double-stranded DNA molecule, as represented by the sequence of positions 7590-8051 from 5'-end of SEQ ID NO. 1 in the sequence listing, was artificially synthesized, designated as arm donor (donor DNA).

A recombinant vector, pCXUN-cas9-gRNA548-gRNA627-arm donor (a circular plasmid) was artificially synthesized. The recombinant vector pCXUN-cas9-gRNA548-gRNA627-arm donor is represented by SEQ ID NO. 1 in the sequence listing. In the SEQ ID NO. 1, the nucleotides at positions 900-7570 constitute a Cas9 protein expression cassette (the nucleotides at positions 5580-7570 constitute a Ubiquitin promoter, the nucleotides at positions 1446-5576 constitute a Cas9 gene, and the nucleotides at positions 900-1152 constitute a NOS terminator), the nucleotides at positions 261-747 constitute a gRNA expression cassette 1 (the nucleotides at positions 367-747 constitute a OsU3 promoter, the nucleotides at positions 271-366 constitute a gRNA1 encoding gene, and the nucleotides at positions 261-270 constitute a Poly-A terminator), the nucleotides at positions 8328-8814 constitute a gRNA expression cassette 2 (the nucleotides at positions 8328-8708 constitute a OsU3 promoter, the nucleotides at positions 8709-8804 constitute a gRNA2 encoding gene, and the nucleotides at positions 8805-8814 constitute a Poly-T terminator), and the nucleotides at positions 7590-8051 constitute an arm donor (the nucleotides at positions 7590-7609 constitute a upstream target site, the nucleotides at positions 7616-7715 constitute a upstream homologous arm, the nucleotides at positions 7716-7979 constitute a fragment for site-specific modification, the nucleotides at positions 7980-8025 constitute a downstream homologous arm, and the nucleotides at positions 8032-8051 constitute a downstream target site). The Cas9 protein expression cassette was used for expression of a Cas9 protein. The gRNA expression cassette 1, designated as expression cassette gRNAW548L, was used for expression of gRNAW548L. The gRNA expression cassette 2, designated as expression cassette gRNAS627I, was used for expression of gRNAS627I.

EXAMPLE 2

Production and Confirmation of Rice with ALS Having Both Amino Acids at Positions 548 and 627 Site-Specifically Modified I. Production of site-specifically modified rice
1. Plump seeds of Nipponbare rice were selected and dehulled. After sterilization and washing, the seeds were uniformly dibbled into solid medium R1, and exposed to continuous illumination at 28° C. for 2-3 weeks to induce the formation of calli.
2. Following step 1, the induced calli were treated with solid medium R1 containing 0.3M mannitol and 0.3M sorbitol for 4-6 h, to obtain treated calli.
3. The recombinant vector pCXUN-cas9-gRNA548-gRNA627-arm donor and the arm-donor were mixed in a molar ratio of 1:20, and the mixture was used to bombard the treated calli obtained in step 2 by means of a biolistic (using gold powder of 0.6 μm, at a bombardment pressure of 900 psi), to obtain transformed calli.
4. After step 3 was completed, the transformed calli were cultured on solid medium R1 containing 0.3M mannitol and 0.3M sorbitol for 16 h, and then transferred onto solid medium R1 containing 50 mg/L hygromycin for culture under light condition at 28° C. for 2 weeks, followed by transferring to solid medium R1 contianing 0.4 μM bispyribac-sodium and culturing at 28° C. under light condition for 2 weeks.
5. After step 4 was completed, well grown, bright yellow, positive calli were selected and transferred into solid medium R4 containing 0.4 μM bispyribac-sodium with sterile tweezers, and subjected to light incubation at 28° C. until differentiated seedlings were grown to 2-5 mm.
6. After step 5 was completed, the seedlings were transferred into solid medium R5 and subjected to light incubation at 28° C. for 2-3 weeks, and then transplanted into soil, and placed in a greenhouse for cultivation (at a temperature of 28-30° C., 16 h illumination/8 h darkness). A total of 116 plants of $T_0$ site-specifically modified rice were obtained, designated as Cas9-arm donor group.
7. The treated calli obtained in step 2 were cultured on solid medium R1 containing 0.3M mannitol and 0.3M sorbitol for 16 h, and then transferred to solid medium R1 and subjected to light incubation at 28° C. for 2 weeks, followed by transfer to solid medium R1 and 2-week 28° C. light incubation.
8. After step 7 was completed, well grown, bright yellow calli was selected and transferred into solid medium R4 with sterile tweezers for 28° C. light incubation, until differentiated seedlings were grown to 2-5 mm.
9. After step 8 was completed, the seedlings were transferred to solid medium R5, and incubated under light at 28° C. for 2-3 weeks, and then transplanted into soil and placed in a greenhouse for cultivation (at a temperature of 28-30° C., 16 h illumination/8 h darkness) to obtain $T_0$ non-site-specifically modified rice, designated as wild-type group.
II. Identification of Homologous Recombinant Plant
10. 1. Identification of homologous recombination plant by PCR and enzyme digestion
52 rice plants from the Cas9-arm donor group and 10 rice plants from the wild-type group obtained in step I were randomly taken for following identification.
Leaves of the rice were collected, from which genomic DNA was extracted using a plant genomic DNA extraction kit (Tiangen Biotech (Beijing) Co., Ltd.). With the genomic DNA as a template, acetolactate synthase (ALS) gene was subjected to PCR amplification using a primer pair consisting of 753F and 753R, followed by identification by enzyme cleavage with a restriction enzyme EcoRV. PCR reaction system (25 μL): 10×PCR Buffer 2.5 μL, dNTP 2 μL, 753F 0.5 μL, 753R 0.5 μL, genomic DNA 1 μL, rTaq 0.2 μL, ddH$_2$O 18.3 μL. PCR reaction conditions: pre-denaturation at 94° C. for 4 min; 35 cycles of denaturation at 94° C. for 40 s, annealing at 58° C. for 40 s, extension at 72° C. for 1 min; finally extension at 72° C. for 10 min.

In view of high homology between arm-Donor and native ALS gene segment of rice, 753F and 753R were positioned upstream and downstream of segment in rice genome corresponding to that in the arm-Donor, respectively so as to eliminate the interference of arm-Donor with the identification of a homologous recombinant plant, since the rice native ALS gene itself contains restriction enzyme EcoRV restriction site (gatatc). Accordingly, a site-specific mutation was introduced into the arm-Donor, so that the PCR amplified products with arm-Donor as a template could be not cleaved by restriction enzyme EcoRV. With the genomic DNA of a plant to be tested as a template, if the PCR amplified product cannot be cleaved by restriction enzyme EcoRV (the PCR amplified product remains 753 bp due to non-cleavage occurred after digestion with restriction enzyme EcoRV), the plant to be tested is a plant that is successfully recombined. With the genomic DNA of a plant to be tested as a template, if the PCR amplified product may be cleaved by restriction enzyme EcoRV (becoming 488 bp and 265 bp), the plant to be tested is a plant that is not successfully recombined.

Agarose gel electrophoresis patterns of a portion of the cleaved products are shown in FIG. 1. Of the 52 rice plants of the Cas9-arm donor group, 48 plants were not cleaved by restriction enzyme EcoRV, and 4 plant were cleaved by restriction enzyme EcoRV. All of the rice plants of the wild-type group were cleaved by restriction enzyme EcoRV.

2. Sequencing

Genomic DNAs were extracted from the 52 rice plants of the Cas9-arm donor group randomly selected in step 1, and subjected to PCR amplification using a primer pair consisting of 753F and 753R, followed by sequencing the PCR amplified products.

Among them, 48 plants which could not be cleaved by restriction enzyme EcoR V were successful homologous recombinant plants (including B98-1, B98-3, B98-4, B98-5, B99-5, B99-6, B99-7, B99-13, and B99-23), and homozygous lines. As compared with wild-type, the successful homologous recombinant plants of the Cas9-arm donor group each had an ALS gene with tryptophan (W) (which has a codon of TGG at this position in wild-type) mutated to leucine (L) (which has a codon of TTG at this position) at position 548, serine (S) (which has a codon of AGT at this position in wild-type) mutated to isoleucine (I) (which has a codon of ATT at this position) at position 627, and other amino acids unchanged, except for synonymous mutation of the nucleotides near these two sites.

The sequencing results suggest that, the 4 rice plants of the Cas9-arm donor group that could be cleaved by restriction enzyme EcoRV (B99-9, B99-10, B99-11 and B99-12) had one strand where homologous recombination occurred at the codon of the 548th amino acid of ALS, but not at the codon of the 627th amino acid of ALS, and the other strand where non-homologous recombination occurred at both the codons of the 548th amino acid and of the 627th amino acid of ALS.

The statistic results of the recombination of the plants of Cas9-arm donor group are shown in Table 2.

TABLE 2

Statistic results of recombination

| No. | Number of plant tested | Line No. | Genotype | Zygosity of $T_0$ plants | Donor DNA in vector | Cas9 | gRNA |
|---|---|---|---|---|---|---|---|
| B97 | 2 | 1, 2 | HR548 & HR627-1 | Ho | deletion | 2+ | 2+ |
| B98 | 24 | 1, 2, 3, 4, 5, 6, 7, 8, 9, 10, 11, 12, 13, 14, 15, 16, 17, 18, 19, 20, 21, 22, 23, 24 | HR548 & HR627-3 | Ho | deletion | 24+ | 24+ |
| B99 | 24 | 1, 2, 3, 4, 13, 14 | HR548 & HR627-1 | Ho | deletion | 6+ | 6+ |
|  |  | 5, 6, 7, 8, 17 | HR548 & HR627-2 | Ho | deletion | 5+ | 5+ |
|  |  | 15, 16, 18, 19, 20, 21, 22, 23, 24 | HR548 & HR627-3 | Ho | deletion | 10+ | 10+ |
|  |  | 9 | HR548/NHEJ | Com-He | deletion & NHEJ | 0 | 1+ |
|  |  | 10, 11, 12 | HR548/NHEJ | Com-He | deletion | 0 | 3+ |
| B100 | 2 | 1, 2 | HR548 & HR627-1 | Ho | deletion | 2+ | 2+ |

Figure 2:
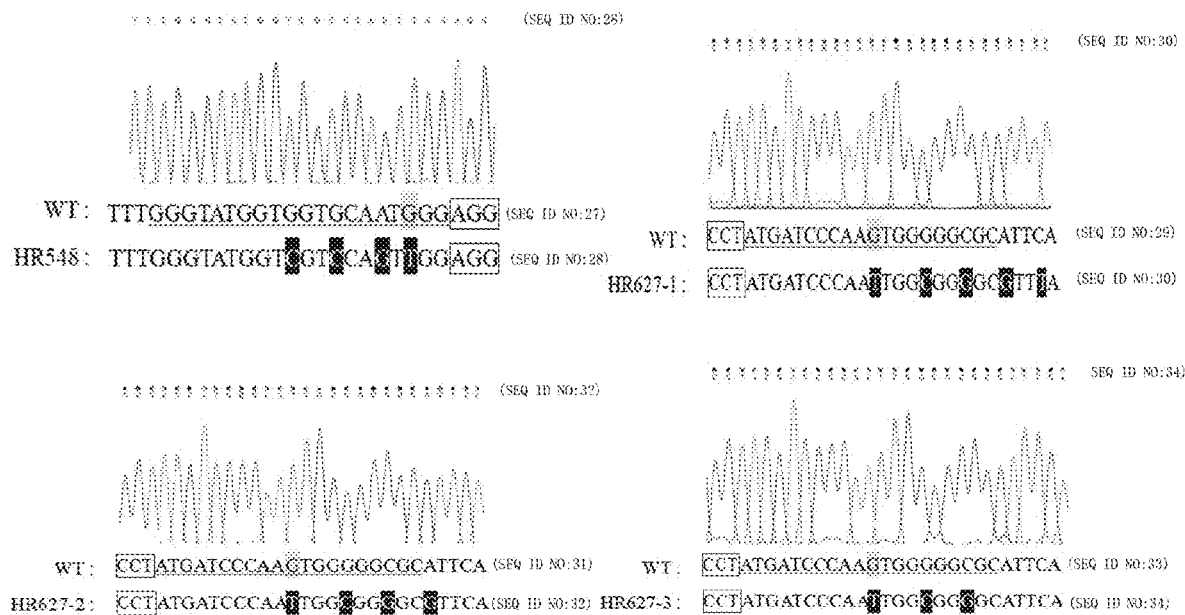
FIG. 2 shows the synonymous mutation results of the nucleotide sequences adjacent to the 548th amino acid and the 627th amino acid of ALS of the plants in Cas9-arm donor group.

Note that: Ho represents a homozygous line, Com-He represents a compound heterozygous line, "+" represents positive result. The sequencing results and corresponding nucleotide sequences of HR548, HR627-1, HR627-2, and HR627-3 are shown in FIG. 2.

Figure 3:
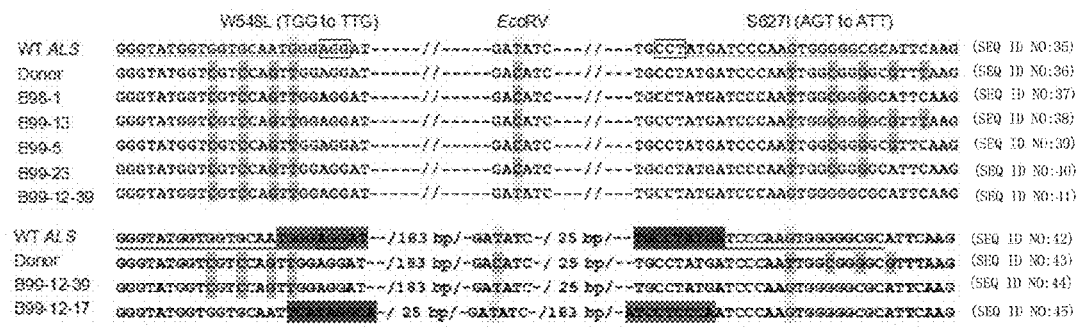
FIG. 3 shows the sequencing identification results of the homologous recombinant type of the plants in Cas9-arm donor group; wherein "WT ALS" represents ALS gene of a wild-type rice plant; and "Donor" represents the gene of donor DNA.

Of part of the plants of the Cas9-arm donor group, the nucleotide sequence adjacent to the 548th amino acid and the nucleotide sequence adjacent to the 627th amino acid are shown in FIG. 3 (B99-12 is a heterozygous type, B99-12-39 and B99-12-17 represent the sequencing results of associated segments of two chromosomes thereof, respectively).

3. Identification of the Presence or Absence of Related Sequence of Recombinant Vector pCXUN-cas9-gRNA548-gRNA627-Arm Donor in Homologous Recombinant Plants According to the sequence of the recombinant vector pCXUN-cas9-gRNA548-gRNA627-arm donor, primer pairs were designed as below, respectively: a primer pair (Cas9-F/Cas9-R) for detecting Cas9 protein gene, with which an amplified fragment of a length of 738 bp can be obtained from a plant containing the Cas9 protein gene; a primer pair (U3F/U3R) for detecting a gRNA expression cassette, with which an amplified fragment of a length of 614 bp can be obtained from a plant containing the gRNA expression cassette; a primer pair (365F/365R) for identifying the intactness of arm donor as an exogenous fragment of randomly integrated recombinant vector pCXUN-cas9-gRNA548-gRNA627-arm donor in a plant, with which an amplified fragments all of a length of 365 bp can be obtained when the arm donors all have been edited in the plant, or an amplified fragments of a length of 841 bp when the arm donors are not edited in the plant, or an amplified fragments of both 365 bp and 841 bp when part of arm donors are edited in the plant.

Figure 4:
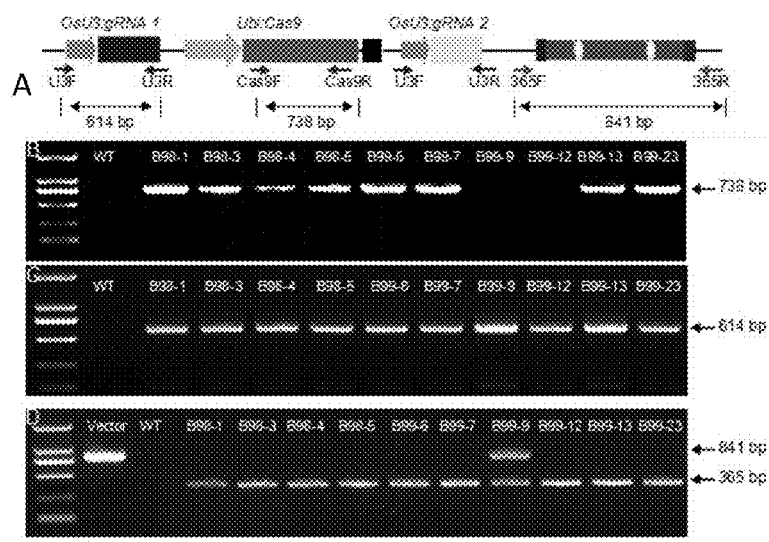
FIG. 4 shows the identification for detecting the presence or absence of related sequences in the recombinant vector pCXUN-cas9-gRNA548-gRNA627-arm donor in the plants of the Cas9-arm donor group; wherein A is a schematic diagram indicating the position of the primers used for the detection in the plants of the Cas9-arm donor group; B is an agarose gel electrophoresis pattern for the detection of the presence or absence of the gene of Cas9 protein in the plants of the Cas9-arm donor group by PCR; C is an agarose gel electrophoresis pattern for the detection of the gRNA expression cassettes in the plants of the Cas9-arm donor group by PCR; and D is an agarose gel electrophoresis pattern for the identification of intactness of the exogenous fragment arm donor in the randomly integrated recombinant vector pCXUN-cas9-gRNA548-gRNA627-arm donor in the plants of the Cas9-arm donor group by PCR, wherein "Vector" represents the recombinant vector pCXUN-cas9-gRNA548-gRNA627-arm donor, and "WT" represents the identification results from the enzyme digestion of the PCR products of rice plants of the wild-type group.

Genomic DNAs were extracted from the 52 rice plants of the Cas9-arm donor group randomly selected in step 1, and subjected to PCR assay using the primer pair for identifying Cas9 protein gene. The results indicate that all the plants contained Cas9 protein gene, i.e., amplified fragments of which have a length of 738 bp in the PCR amplification products, except for plants B99-9, B99-10, B99-11 and B99-12. All the plants containing Cas9 protein gene exhibited successful homologous recombination, and belonged to homozygous lines, so that the gRNA could not recognize site-specifically modified ALS gene, with no occurrence of chimera. The 4 plants, B99-9, B99-10, B99-11 and B99-12, although having unedited position 627 of ALS, could not be re-edited due to the absence of the intact sequence of Cas9 protein gene (FIG. 4, B).

Genomic DNAs were extracted from the 52 rice plants of the Cas9-arm donor group randomly selected in step 1, and subjected to PCR assay using the primer pairs for identifying gRNA expression cassettes. The identification results indicate that all the plants contained the gRNA expression cassette (FIG. 4, C), and all the PCR amplification products contained the amplified fragment of a 614 bp length.

Genomic DNAs were extracted from the 52 rice plants of the Cas9-arm donor group randomly selected in step 1, and subjected to PCR assay using the primer pair for identifying the intactness of the exogenous fragment arm donor in the recombinant vector pCXUN-cas9-gRNA548-gRNA627-arm donor randomly integrated in the detected plant. The identification results indicate that 51 out of the 52 plants were big fragment deficient type. That is, all the exogenous fragment, arm donor, had been edited by the designed recombinant vector pCXUN-cas9-gRNA548-gRNA627-arm donor, wherein the presence of gRNA548 and gRNA627 allowed the exogenous fragment, arm donor, to be cleaved and used for site-specifically modifying the native ALS gene of the rice, resulting in a large fragment deficient type. And, plant B99-9 was the only one with PCR amplification products of 841 bp long fragment (FIG. 4, D). The sequencing results indicate that this plant had non-homologous recombination occurring at the codons of both the 548th and 627th amino acids of ALS.

4. Off-Target Analysis of Recombinant Vector pCXUN-cas9-gRNA548-gRNA627-Arm Donor By means of an online prediction software, off-target sites that might exist in gRNA548 and gRNA627 were pedicted, respectively, primer pairs were designed depending on the sequences flanking the off-target sites that might exist: the primer pairs for gRNAW548L expression cassette were OFF1F/OFF1R and OFF2F/OFF2R, and the primer pairs for gRNAS627I expression cassette were OFF3F/OFF3R, OFF4F/OFF4R and OFF5F/OFF5R.

Genomic DNAs were extracted from the 52 rice plants of the Cas9-arm donor group randomly selected in step 1, and subjected to PCR identification using each of the primer pair described above, respectively. The primer pairs OFF1F/OFF1R, OFF2F/OFF2R, OFF3F/OFF3R, OFF4F/OFF4R and OFF5F/OFF5R resulted in amplified fragment lengths of 492 bp, 606 bp, 597 bp, 388 bp and 382 bp for off-target plants.

30 plants were PCR amplified with primer pairs OFF1F/R, OFF2F/R, OFF3F/R, OFF4F/R and OFF5F/R, and the PCR amplification products were cloned and sequenced. The detection results indicated that the designed recombinant vector pCXUN-cas9-gRNA548-gRNA627-arm donor led to gRNA expression, and the expressed gRNA did not have off-target (Table 3).

TABLE 3

Off-target analysis of target spot

| Target spot | Name of target | Position of target | Sequence of target | Number of mis-matched bases | Number of plants tested | Number of off-target plants detected |
|---|---|---|---|---|---|---|
| gRNA W548L | OFF1 | chr04: 19170867- 19170889 | SEQ ID NO: 22 GGGCATGGTGGTGCA GTGGGAGG | 2 | 30 | 0 |
| | OFF2 | chr03: 1562250- 1562272 | SEQ ID NO: 23 GGGTGTGGTGCTGCA TTGGGTGG | 2 | 30 | 0 |
| gRNAS 627I | OFF3 | chr09: 15887010- 15887031 | SEQ ID NO: 24 G_GCCACCACTGGG GATCATTGG | 3 | 30 | 0 |
| | OFF4 | chr01: 36565231- 36565253 | SEQ ID NO: 25 CCGGTGCTCCCAGGT GGGAGCGC | 4 | 30 | 0 |
| | OFF5 | chr10: 17913749- 17913771 | SEQ ID NO: 26 GAGCCCCACGTGGG AGCAACGG | 4 | 30 | 0 |

4. Identification of Resistance of Plant with Successful Homologous Recombination to Herbicide Bispyribac-Sodium (BS)

The wild-type rice, and the $T_0$ site-specifically modified rice of the Cas9-arm donor group with successful homologous recombination at the codons of both the 548th and 627th amino acids of ALS as obtained in step I were sprayed with Bispyribac-sodium in a concentration of 100 μM, and 30-50 days thereafter, the growth states of the plants were observed.

Figure 5:
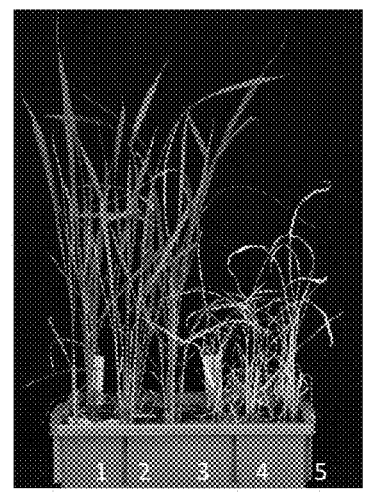
FIG. 5 shows the plant growth 36 days after spraying Bispyribac-sodium; wherein "1", "2" and "3" each represent a plant having successful homologous recombination at two sites, and "4", "5" and "6" each represent a rice plant of wild-type.

The results were shown in FIG. 5. 36 days after the spray of the Bispyribac-sodium in the concentration of 100 μM, the wild-type rice plants were withered, while the $T_0$ site-specifically modified, successfully homologous recombinant plants of the Cas9-arm donor group showed normal growth.

INDUSTRIAL APPLICATION

The present invention develops a technical system for producing an herbicide-resistant rice by site-specifically modifying acetolactate synthase (ALS) gene using a CRISPR/Cas9 system, and provides a basis for gene site-specific modification, replacement, and exogenous gene site-specific integration in rice and other crops using the CRISPR/Cas9 system, and a support for improving agronomic traits of other important crops.

SEQUENCE LISTING

```
<160> NUMBER OF SEQ ID NOS: 45

<210> SEQ ID NO 1
<211> LENGTH: 17778
<212> TYPE: DNA
<213> ORGANISM: Artificial sequence
<220> FEATURE:
<223> OTHER INFORMATION: recombinant vector pCXUN-cas9-gRNA548-gRNA627-
      arm donor

<400> SEQUENCE: 1
gaattcgagc tcggtaccgc tgtgccgtac gacggtacga ggtacgagca ggtcagcggg        60
tcaccagtgt tgtgtgaagc caagctgtat tcactagctc gggatagttg gcacaaacgg       120
catgaaaatg tggcgccgta aataagtgaa atacagctgc gtactttttg aacacgctgc       180
aaacatgaga cggagaaatt tcaatgcaaa acggaaaata aaactgcaaa catgcgacgg       240
agaaaactca atgcaaaacg aaaaaaaaaa gcaccgactc ggtgccactt tttcaagttg       300
ataacggact agccttattt taacttgcta tttctagctc taaaacccca ttgcaccacc       360
ataccctgcc acggatcatc tgcacaactc ttttaaatca gctttgatct atgtggatag       420
ccgaggtggt actaatacta gtctttgttg tcgtccaatt gcgtaatggg ccggcccata       480
ctgcaataca tgtcctgaaa ggcttcatgg cccactacga aatgcttttc tcctacagtt       540
```

```
tatcttactt cttcacatca cgtggtttcc aacgtaccca gtgttccggg cttccagcat    600
ttgctggtag caccagtaga agacgcctgt cttgtgctat ggtccctgac tgcacatctg    660
attcctccaa gatccatgca tgcctgataa ctttaagttg cttcagaaga actttaagtg    720
atctgttcgt atgtttaaag attccttgat aaaataagtt gcagttctga aaatcctaga    780
acttggagac ctggatgaat taccctggcg aaaggggat gtgctgcaag gcgattaagt    840
tgggtaacgc cagggttttc ccagtcacga cgttgtaaaa cgacggccag tgaattcccg    900
atctagtaac atagatgaca ccgcgcgcga taatttatcc tagtttgcgc gctatatttt    960
gttttctatc gcgtattaaa tgtataattg cgggactcta atcataaaaa cccatctcat    1020
aaataacgtc atgcattaca tgttaattat tacatgctta acgtaattca acagaaatta    1080
tatgataatc atcgcaagac cggcaacagg attcaatctt aagaaacttt attgccaaat    1140
gtttgaacga tcgggaaat tcggatcccc aatacttgta tgggtcgacc tgcagactgg    1200
ctgtgtataa gggagcctga catttatatt ccccagaaca tcaggttaat ggcgttttg    1260 atgtcatttt cgcggtggct gagatcagcc acttcttccc cgataacgga gaccggcaca    1320
ctggccatat cggtggtcat catgcgccag ctttcatccc cgatatgcac caccgggtaa    1380
agttcacggg agactttatc tgacagcaga cgtgcactgg ccaggggat caccatccgt    1440 cgccctcaat cgccgccgag ttgtgagagg tcgatgcgtg tctcgtagag gcctgtgata    1500
gactggtgga tgagggtggc gtcgagaacc tccttggtag aggtgtagcg cttgcggtcg    1560
atggtggtgt cgaagtactt gaaggcggct ggagcgccga ggttggtgag ggtgaagagg    1620
tggatgatgt tctcggcctg ctcgcgaatt ggcttatcgc ggtgcttgtt gtaggcgctg    1680
agcaccttat cgaggttggc atcggcgagg atcacgcgct tggagaactc ggagatctgc    1740
tcgatgatct cgtcgaggta gtgcttgtgc tgctcgacga acagctgctt ttgctcgttg    1800
tcctctgggg agcccttgag cttctcgtag tgggaggcga ggtagaggaa gttcacgtac    1860
ttggacggga gagcaagctc gttgcccttc tgaagctcgc cagcagaggc gagcattctc    1920
ttgcggccgt tctcaagctc gaagaggctg tacttcggga gcttgatgat gaggtccttc    1980
ttcacctcct tgtagcccct tggcctcgagg aagtcgattg ggttcttctc gaagctgctg    2040
cgctccatga tcgtgatgcc cagcagctcc ttgacggact tgagcttctt gctcttgccc    2100
ttctcgacct tggcaaccac gagcacagag taggccacgg tcggagaatc gaagccgcca    2160
tacttcttcg ggtcccagtc cttcttgcgg gcgatcagct tgtcggagtt gcgctttggg    2220
aggatggact ccttggagaa gccgccggtc tgaacctcgg tcttcttcac gatgttcact    2280
tgcggcatgg agagcacctt gcgcactgtg gcgaaatccc tgcccttgtc ccacacgatc    2340
tcgcctgtct cgccgtttgt ctcgatgagc ggcctcttcc taatctcgcc gttggcgagc    2400
gtgatctcgg tcttgaagaa attcatgatg ttggagtaga agaagtactt ggcggtcgcc    2460
ttgccgatct cttgctcgga cttggcgatc atcttgcgca cgtcgtacac cttgtagtcg    2520
ccgtacacga actcggactc gagctttggg tacttcttga tgagggctgt gcccaccacg    2580
gcattgaggt aggcgtcgtg ggcgtggtgg tagttgttga tctcgcgcac cttgtagaac    2640
tggaagtcct tgcggaagtc ggacacgagc ttggacttga gggtgatgac cttcacctcg    2700
cggatgagct tgtcgttctc gtcgtacttg tgttcatgc gggagtcgag gatctgggcc    2760
acgtgctttg tgatctggcg tgtctcgacg agctggcgct tgatgaagcc ggccttatca    2820
agctcggaaa ggccgcctct ctcggccttg gtgaggttgt cgaacttcct ctgggtgatg    2880
```

```
agcttggcgt tgaggagctg gcgccagtag ttcttcatct tcttgacgac ctcttcggac    2940
ggcacgttat cggacttgcc cctgttcttg tcggagcggg tgagcacctt gttgtcgatg    3000
gagtcgtcct tcaggaagga ctgcggcaca atatggtcca cgtcgtagtc ggagaggcgg    3060
ttgatgtcca gctcttggtc cacgtacatg tcgcggccgt tctggaggta gtagaggtag    3120
agcttctcgt tctggagctg ggtgttctcg actgggtgct ccttgaggat ctgggagccc    3180
agctccttaa tgccctcctc gatcctcttc atgcgctcgc gggagttctt ttggcccttc    3240
tgtgtggtct ggttctcgcg ggccatctcg atcacgatgt tctctggctt gtgcctgccc    3300
atcaccttca ccagctcgtc caccaccttc acggtctgga gaatgcccct tcttgatagcc   3360 ggggagccgg cgagattggc gatatgctca tggagggaat cgccttggcc ggacacctgg    3420
gccttttgga tgtcctcctt gaaggtgagg gagtcgtcgt ggatgagctg catgaagttg    3480
cggttggcga agccgtcgga cttgaggaag tcgaggatcg tcttgccgga ctgcttgtcg    3540
cggatgccgt tgatgagctt cctagagagc ctgccccagc cggtatagcg cctgcgcttc    3600
agctgcttca tcaccttgtc gtcgaagagg tgggcgtatg tcttgaggcg ctcctcgatc    3660
atctcgcggt cctcgaagag ggtgagggtg agcacgatgt cctcgaggat gtcctcgttc    3720
tcctcgttgt cgaggaagtc cttgtccttg ataatcttga ggaggtcgtg gtaggtcccg    3780
agggaggcat tgaacctatc ctcgacgccg gagatctcga cggagtcgaa gcactcgatt    3840
ttcttgaagt agtcctcctt gagctgcttc acggtcacct gcggttggt cttgaacagc     3900 aggtcgacga tggccttctt ttgctcgccg ctaaggaaag ctggcttcct catcccctcg    3960
gtcacgtact tcaccttggt cagctcgttg tacacggtga agtactcgta gaggagtgag    4020
tgcttcggga gcaccttctc gttcgggagg ttcttgtcga agttggtcat gcgctcgatg    4080
aaagactggg cagaggcgcc cttatccacc acctcctcga agttccaggg ggtgattgtc    4140
tcctcggact ttctggtcat ccaggcgaac ctggagttgc cctggcgag cgggcccacg     4200 tagtacggga tgcggaaggt gaggatcttc tcaatcttct cgcggttgtc cttgaggaac    4260
gggtagaagt cctcttgcct gcggaggata gcatgaagct cgccgaggtg gatctggtgc    4320
gggatggagc cattatcgaa ggtgcgctgc ttgcggagga ggtcctctct attgagcttc    4380
acgagcagct cctcggtgcc gtccatcttc tcgaggatcg gcttgatgaa cttgtagaac    4440
tcctcttgag aagcgccgcc atcgatgtag ccggcgtagc cgttcttgga ctggtcgaag    4500
aagatctcct tgtacttctc tgggagctgc tgtctcacga gggccttgag gagtgtgagg    4560
tcctggtggt gctcgtcgta cctcttgatc atggaggcgg agagtggggc cttggtgatc    4620
tcggtgttca ccctgaggat gtcgctgagg aggatggcgt cggagagatt cttggcggcg    4680
aggaacagat cggcgtactg atcgccaatc tgggcgagga gattgtcgag gtcgtcgtcg    4740
taggtgtcct tggaaagctg gagcttggcg tcctcggcga ggtcgaagtt ggacttgaag    4800
ttcggggtga ggccaagaga gagggcgatc aggttgccga agaggccatt cttcttctcg    4860
cccggaagtt gggcgatcag attctcgagc ctgcggact tagagagcct ggcagagaga     4920
atagccttgg cgtcaacgcc agaggcgttg atcgggttct cctcgaacag ctggttgtag    4980
gtctgcacga gctggatgaa cagcttgtcc acatccgagt tgtccgggtt gaggtcgccc    5040
tcgatgagga agtggcccct gaacttgatc atgtgggcga gggcgaggta gatgagcctg    5100
aggtcggcct tatcggtgga gtcgacgagc ttcttgcgga ggtggtagat ggtcgggtac    5160
ttctcgtggt aggccacctc atccacgatg ttgccgaaga tcggatggcg ctcgtgcttc    5220
ttgtcctcct cgacgaggaa gctctcctcg agcctgtgga agaagctgtc gtccaccttg    5280
```

```
gccatctcgt tggagaagat ctcttggagg tagcagatgc ggttcttgcg cctggtgtac    5340
ctgcgtctag cggtcctctt gagccttgta gcctcggctg tctcgccaga gtcgaacagc    5400
agggcgccga tgagattctt cttgatggag tggcggtcgg tgttgccgag gaccttgaac    5460
ttcttggacg gcaccttgta ctcgtcggtg atcacggccc agccaacaga attggtgccg    5520
atgtcgaggc cgatggagta cttcttgtcg accttgcgct tcttctttgg ggccatgggc    5580
tgcagaagta acaccaaaca acagggtgag catcgacaaa agaaacagta ccaagcaaat    5640
aaatagcgta tgaaggcagg gctaaaaaaa tccacatata gctgctgcat atgccatcat    5700
ccaagtatat caagatcaaa ataattataa aacatacttg tttattataa tagataggta    5760
ctcaaggtta gagcatatga atagatgctg catatgccat catgtatatg catcagtaaa    5820
acccacatca acatgtatac ctatcctaga tcgatatttc catccatctt aaactcgtaa    5880
ctatgaagat gtatgacaca cacatacagt tccaaaatta ataaatacac caggtagttt    5940
gaaacagtat tctactccga tctagaacga atgaacgacc gcccaaccac accacatcat    6000
cacaaccaag cgaacaaaaa gcatctctgt atatgcatca gtaaaacccg catcaacatg    6060
tatacctatc ctagatcgat atttccatcc atcatcttca attcgtaact atgaatatgt    6120
atggcacaca catacagatc caaaattaat aaatccacca ggtagtttga aacagaattc    6180
tactccgatc tagaacgacc gcccaaccag accacatcat cacaaccaag acaaaaaaaa    6240
gcatgaaaag atgacccgac aaacaagtgc acggcatata ttgaaataaa ggaaaagggc    6300
aaaccaaacc ctatgcaacg aaacaaaaaa aatcatgaaa tcgatcccgt ctgcggaacg    6360
gctagagcca tcccaggatt ccccaaagag aaacactggc aagttagcaa tcagaacgtg    6420
tctgacgtac aggtcgcatc cgtgtacgaa cgctagcagc acggatctaa cacaaacacg    6480
gatctaacac aaacatgaac agaagtagaa ctaccgggcc ctaaccatgg accggaacgc    6540
cgatctagag aagtagaga gggggggggg gggaggacga gcggcgtacc ttgaagcgga    6600
ggtgccgacg ggtggatttg ggggagatct ggttgtgtgt gtgtgcgctc cgaacaacac    6660
gaggttgggg aaagagggtg tggaggggggt gtctatttat tacggcgggc gaggaaggga    6720
aagcgaagga gcggtgggaa aggaatcccc cgtagctgcc gtgccgtgag aggaggagga    6780
ggccgcctgc cgtgccggct cacgtctgcc gctccgccac gcatttctgg atgccgacag    6840
cggagcaagt ccaacggtgg agcggaactc tcgagagggg tccagaggca gcgacagaga    6900
tgccgtgccg tctgcttcgc ttggcccgac gcgacgctgc tggttcgctg gttggtgtcc    6960
gttagactcg tcgacggcgt ttaacaggct ggcattatct actcgaaaca agaaaaatgt    7020
ttccttagtt ttttttaattt cttaagggt atttgtttaa ttttttagtca ctttattttta   7080 ttctatttta tatctaaatt attaaataaa aaaactaaaa tagagtttta gttttcttaa    7140
tttagaggct aaaatagaat aaaatagatg tactaaaaaa attagtctat aaaaaccatt    7200
aaccctaaac cctaaatgga tgtactaata aaatggatga agtattatat aggtgaagct    7260
atttgcaaaa aaaaggaga acacatgcac actaaaaaga taaaactgta gagtcctgtt    7320
gtcaaaatac tcaattgtcc tttagaccat gtctaactgt tcatttatat gattctctaa    7380
aacactgata ttattgtagt actatagatt atattattcg tagagtaaag tttaaatata    7440
tgtataaaga tagataaact gcacttcaaa caagtgtgac aaaaaaaata tgtggtaatt    7500
ttttataact tagacatgca atgctcatta tctctagaga ggggcacgac cgggtcacgc    7560
tgcactgcag gaattcgata tcaacatttg ggtatggtgg tgcaatggga ggatattgat    7620
```

```
gggatggta gcttcctcat gaacattcag gagctggcat tgatccgcat tgagaacctc   7680
cctgtgaagg tgatggtgtt gaacaaccaa catttgggta tggtcgtcca gttggaggat   7740
aggttttaca aggcgaatag ggcgcataca tacttgggca acccggaatg tgagagcgag   7800
atatatccag attttgtgac tattgctaag gggttcaata ttcctgcagt ccgtgtaaca   7860
aagaagagtg aagtccgtgc cgccatcaag aagatgctcg agactccagg ccatacttg    7920 ttggacatca tcgtcccgca ccaggagcat gtgctgccta tgatcccaat tggcggggcg   7980
tttaaggaca tgatcctgga tggtgatggc aggactgtgt attaattgaa tgcgccccca   8040
cttgggatca taggcagcaa gcttggcact ggccgtcgtt ttacaacgtc gtgactggga   8100
aaaccctggc gttacccaac ttaatcgcct tgcagcacat cccccttttcg ccagctggcg   8160 taatagcgaa gaggcccgca ccgatcgccc ttcccaacag ttgcgcagcc tgaatggcga   8220
atgctagagc agcttgagct tggatcagat tgtcgtttcc cgccttcagt tgtaattcat   8280
ccaggtctcc aagttctagg attttcagaa ctgcaactta ttttatcaag gaatctttaa   8340
acatacgaac agatcactta aagttcttct gaagcaactt aaagttatca ggcatgcatg   8400
gatcttggag gaatcagatg tgcagtcagg gaccatagca caagacaggc gtcttctact   8460
ggtgctacca gcaaatgctg gaagccggga acactgggta cgttggaaac cacgtgatgt   8520
gaagaagtaa gataaactgt aggagaaaag catttcgtag tgggccatga agcctttcag   8580
gacatgtatt gcagtatggg ccggcccatt acgcaattgg acgacaacaa agactagtat   8640
tagtaccacc tcggctatcc acatagatca aagctgattt aaaagagttg tgcagatgat   8700
ccgtggcagc gccccacctt gggatcatgt tttagagcta gaaatagcaa gttaaaataa   8760
ggctagtccg ttatcaactt gaaaaagtgg caccgagtcg gtgcttttt ttttcgtttt    8820 gcattgagtt ttctccgtcg catgtttgca gttttatttt ccgttttgca ttgaaatttc    8880
tccgtctcat gtttgcagcg tgttcaaaaa gtacgcagct gtatttcact tatttacggc   8940
gccacatttt catgccgttt gtgccaacta tcccgagcta gtgaatacag cttggcttca   9000
cacaacactg gtgacccgct gacctgctcg tacctcgtac cgtcgtacgg cacagcattt   9060
ggaattaaag ggtgtgatcg atactgtaaa ctatcagtgt ttgacaggat atattggcgg   9120
gtaaacctaa gagaaaagag cgtttattag aataacggat atttaaaagg gcgtgaaaag   9180
gtttatccgt tcgtccattt gtatgtgcat gccaaccaca gggttcccct cgggatcaaa   9240
gtactttgat ccaacccctc cgctgctata gtgcagtcgg cttctgacgt tcagtgcagc   9300
cgtcttctga aaacgacatg tcgcacaagt cctaagttac gcgacaggct gccgccctgc   9360
ccttttcctg gcgttttctt gtcgcgtgtt ttagtcgcat aaagtagaat acttgcgact   9420
agaaccggag acattacgcc atgaacaaga gcgccgccgc tggcctgctg ggctatgccc   9480
gcgtcagcac cgacgaccag gacttgacca accaacgggc cgaactgcac gcggccggct   9540
gcaccaagct gttttccgag aagatcaccg gcaccaggcg cgaccgcccg gagctggcca   9600
ggatgcttga ccacctagcc ctggcgacgt tgtgacagtg accaggctag accgcctggc   9660
ccgcagcacc cgcgacctac tggacattgc cgagcgcatc caggaggccg gcgcgggcct   9720
gcgtagcctg gcagagccgt gggccgacac caccacgccg gccggccgca tggtgttgac   9780
cgtgttcgcc ggcattgccg agttcgagcg ttccctaatc atcgaccgca cccggagcgg   9840
gcgcgaggcc gccaaggccc gaggcgtgaa gtttggcccc cgccctaccc tcaccccggc   9900
acagatcgcg cacgcccgcg agctgatcga ccaggaaggc cgcaccgtga agaggcggc    9960 tgcactgctt ggcgtgcatc gctcgaccct gtaccgcgca cttgagcgca gcgaggaagt   10020
```

```
gacgcccacc gaggccaggc ggcgcggtgc cttccgtgag gacgcattga ccgaggccga    10080
cgccctggcg gccgccgaga atgaacgcca agaggaacaa gcatgaaacc gcaccaggac    10140
ggccaggacg aaccgttttt cattaccgaa gagatcgagg cggagatgat cgcggccggg    10200
tacgtgttcg agccgcccgc gcacgtctca accgtgcggc tgcatgaaat cctggccggt    10260
ttgtctgatg ccaagctggc ggcctggccg gccagcttgg ccgctgaaga aaccgagcgc    10320
cgccgtctaa aaaggtgatg tgtatttgag taaaacagct tgcgtcatgc ggtcgctgcg    10380
tatatgatgc gatgagtaaa taaacaaata cgcaagggga acgcatgaag gttatcgctg    10440
tacttaacca gaaaggcggg tcaggcaaga cgaccatcgc aacccatcta gcccgcgccc    10500
tgcaactcgc cggggccgat gttctgttag tcgattccga tccccagggc agtgcccgcg    10560
attgggcggc cgtgcgggaa gatcaaccgc taaccgttgt cggcatcgac cgcccgacga    10620
ttgaccgcga cgtgaaggcc atcggccggc gcgacttcgt agtgatcgac ggagcgcccc    10680
aggcggcgga cttggctgtg tccgcgatca aggcagccga cttcgtgctg attccggtgc    10740
agccaagccc ttacgacata tgggcaaccg ccgacctggt ggagctggtt aagcagcgca    10800
ttgaggtcac ggatggaagg ctacaagcgg cctttgtcgt gtcgcgggcg atcaaaggca    10860
cgcgcatcgg cggtgaggtt gccgaggcgc tggccgggta cgagctgccc attcttgagt    10920
cccgtatcac gcagcgcgtg agctacccag gcactgccgc cgccggcaca accgttcttg    10980
aatcagaacc cgagggcgac gctgcccgcg aggtccaggc gctggccgct gaaattaaat    11040
caaaactcat ttgagttaat gaggtaaaga gaaaatgagc aaaagcacaa acacgctaag    11100
tgccggccgt ccgagcgcac gcagcagcaa ggctgcaacg ttggccagcc tggcagacac    11160
gccagccatg aagcgggtca actttcagtt gccggcggag gatcacacca gctgaagat     11220 gtacgcggta cgccaaggca agaccattac cgagctgcta tctgaataca tcgcgcagct    11280
accagagtaa atgagcaaat gaataaatga gtagatgaat tttagcggct aaaggaggcg    11340
gcatggaaaa tcaagaacaa ccaggcaccg acgccgtgga atgccccatg tgtggaggaa    11400
cgggcggttg gccaggcgta agcggctggg ttgtctgccg gccctgcaat ggcactggaa    11460
cccccaagcc cgaggaatcg gcgtgacggt cgcaaaccat ccggcccggt acaaatcggc    11520
gcggcgctgg gtgatgacct ggtggagaag ttgaaggccg cgcaggccgc ccagcggcaa    11580
cgcatcgagg cagaagcacg ccccggtgaa tcgtggcaag cggccgctga tcgaatccgc    11640
aaagaatccc ggcaaccgcc ggcagccggt gcgccgtcga ttaggaagcc gcccaagggc    11700
gacgagcaac cagatttttt cgttccgatg ctctatgacg tgggcacccg cgatagtcgc    11760
agcatcatgg acgtggccgt tttccgtctg tcgaagcgtg accgacgagc tggcgaggtg    11820
atccgctacg agcttccaga cgggcacgta gaggtttccg cagggccggc cggcatggcc    11880
agtgtgtggg attacgacct ggtactgatg gcggtttccc atctaaccga atccatgaac    11940
cgataccggg aagggaaggg agacaagccc ggccgcgtgt tccgtccaca cgttgcggac    12000
gtactcaagt tctgccggcg agccgatggc ggaaagcaga aagacgacct ggtagaaacc    12060
tgcattcggt taaacaccac gcacgttgcc atgcagcgta cgaagaaggc caagaacggc    12120
cgcctggtga cggtatccga gggtgaagcc ttgattagcc gctacaagat cgtaaagagc    12180
gaaaccgggc ggccggagta catcgagatc gagctagctg attggatgta ccgcgagatc    12240
acagaaggca agaacccgga cgtgctgacg gttcaccccg attacttttt gatcgatccc    12300
ggcatcggcc gttttctcta ccgcctggca cgccgcgccg caggcaaggc agaagccaga    12360
```

```
tggttgttca agacgatcta cgaacgcagt ggcagcgccg gagagttcaa gaagttctgt    12420
ttcaccgtgc gcaagctgat cgggtcaaat gacctgccgg agtacgattt gaaggaggag    12480
gcggggcagg ctggcccgat cctagtcatg cgctaccgca acctgatcga gggcgaagca    12540
tccgccggtt cctaatgtac ggagcagatg ctagggcaaa ttgccctagc aggggaaaaa    12600
ggtcgaaaag gtctctttcc tgtggatagc acgtacattg ggaacccaaa gccgtacatt    12660
gggaaccgga acccgtacat tgggaaccca agccgtaca ttgggaaccg gtcacacatg     12720
taagtgactg atataaaaga gaaaaaggc gattttttccg cctaaaactc tttaaaactt    12780
attaaaactc ttaaaacccg cctggcctgt gcataactgt ctggccagcg cacagccgaa    12840
gagctgcaaa aagcgcctac ccttcggtcg ctgcgctccc tacgcccgc cgcttcgcgt     12900 cggcctatcg cggccgctgg ccgctcaaaa atggctggcc tacggccagg caatctacca    12960
gggcgcggac aagccgcgcc gtcgccactc gaccgccggc gcccacatca aggcaccctg    13020
cctcgcgcgt ttcggtgatg acggtgaaaa cctctgacac atgcagctcc cggagacggt    13080
cacagcttgt ctgtaagcgg atgccgggag cagacaagcc cgtcagggcg cgtcagcggg    13140
tgttggcggg tgtcggggcg cagccatgac ccagtcacgt agcgatagcg gagtgtatac    13200
tggcttaact atgcggcatc agagcagatt gtactgagag tgcaccatat gcggtgtgaa    13260
ataccgcaca gatgcgtaag gagaaaatac cgcatcaggc gctcttccgc ttcctcgctc    13320
actgactcgc tgcgctcggt cgttcggctg cggcgagcgg tatcagctca ctcaaaggcg    13380
gtaatacggt tatccacaga atcaggggat aacgcaggaa agaacatgtg agcaaaaggc    13440
cagcaaaagg ccaggaaccg taaaaaggcc gcgttgctgg cgttttttcca taggctccgc    13500 cccccctgacg agcatcacaa aaatcgacgc tcaagtcaga ggtggcgaaa cccgacagga    13560
ctataaagat accaggcgtt tccccctgga agctccctcg tgcgctctcc tgttccgacc    13620
ctgccgctta ccggatacct gtccgccttt ctcccttcgg aagcgtggc gctttctcat     13680 agctcacgct gtaggtatct cagttcggtg taggtcgttc gctccaagct gggctgtgtg    13740
cacgaacccc ccgttcagcc cgaccgctgc gccttatccg gtaactatcg tcttgagtcc    13800
aacccggtaa gacacgactt atcgccactg gcagcagcca ctggtaacag gattagcaga    13860
gcgaggtatg taggcggtgc tacagagttc ttgaagtggt ggcctaacta cggctacact    13920
agaaggacag tatttggtat ctgcgctctg ctgaagccag ttaccttcgg aaaaagagtt    13980
ggtagctctt gatccggcaa acaaaccacc gctggtagcg gtggtttttt tgtttgcaag    14040
cagcagatta cgcgcagaaa aaaggatct caagaagatc ctttgatctt ttctacgggg     14100
tctgacgctc agtggaacga aaactcacgt taagggattt tggtcatgca ttctaggtac    14160
taaaacaatt catccagtaa aatataatat tttattttct cccaatcagg cttgatcccc    14220
agtaagtcaa aaaatagctc gacatactgt tcttccccga tatcctccct gatcgaccgg    14280
acgcagaagg caatgtcata ccacttgtcc gccctgccgc ttctcccaag atcaataaag    14340
ccacttactt tgccatcttt cacaaagatg ttgctgtctc ccaggtcgcc gtgggaaaag    14400
acaagttcct cttcgggctt ttccgtcttt aaaaaatcat acagctcgcg cggatcttta    14460
aatggagtgt cttcttccca gttttcgcaa tccacatcgg ccagatcgtt attcagtaag    14520
taatccaatt cggctaagcg gctgtctaag ctattcgtat agggacaatc cgatatgtcg    14580
atggagtgaa agagcctgat gcactccgca tacagctcga taatcttttc agggctttgt    14640
tcatcttcat actcttccga gcaaaggacg ccatcggcct cactcatgag cagattgctc    14700
cagccatcat gccgttcaaa gtgcaggacc tttggaacag gcagctttcc ttccagccat    14760
```

```
agcatcatgt cctttttccg ttcaacatca taggtggtcc ctttataccg gctgtccgtc   14820 attttttaaat ataggttttc attttctccc accagcttat ataccttagc aggagacatt   14880
ccttccgtat cttttacgca gcggtatttt tcgatcagtt ttttcaattc cggtgatatt   14940
ctcattttag ccatttatta tttccttcct cttttctaca gtatttaaag ataccccaag   15000
aagctaatta taacaagacg aactccaatt cactgttcct tgcattctaa aaccttaaat   15060
accagaaaac agcttttttca aagttgtttt caaagttggc gtataacata gtatcgacgg   15120
agccgatttt gaaaccgcgg tgatcacagg cagcaacgct ctgtcatcgt tacaatcaac   15180 atgctacccct ccgcgagatc atccgtgttt caaacccggc agcttagttg ccgttcttcc   15240
gaatagcatc ggtaacatga gcaaagtctg ccgccttaca acggctctcc cgctgacgcc   15300
gtcccggact gatgggctgc ctgtatcgag tggtgatttt tgtgccgagct gccggtcggg   15360 gagctgttgg ctggctggtg gcaggatata ttgtggtgta aacaaattga cgcttagaca   15420
acttaataac acattgcgga cgttttttaat gtactgaatt aacgccgaat taattcgggg   15480
gatctggatt ttagtactgg attttggttt taggaattag aaattttatt gatagaagta   15540
ttttacaaat acaaatacat actaaggggtt tcttatatgc tcaacacatg agcgaaaccc   15600
tataggaacc ctaattccct tatctgggaa ctactcacac attattatgg agaaactcga   15660
gcttgtcgat cgacagatcc ggtcggcatc tactctatttt ctttgccctc ggacgagtgc   15720 tgggcgtcg gtttccacta tcggcgagta cttctacaca gccatcggtc cagacggccg   15780
cgcttctgcg ggcgatttgt gtacgcccga cagtcccggc tccggatcgg acgattgcgt   15840
cgcatcgacc ctgcgcccaa gctgcatcat cgaaattgcc gtcaaccaag ctctgataga   15900
gttggtcaag accaatgcgg agcatatacg cccggagtcg tggcgatcct gcaagctccg   15960
gatgcctccg ctcgaagtag cgcgtctgct gctccataca agccaaccac ggcctccaga   16020
agaagatgtt ggcgacctcg tattgggaat ccccgaacat cgcctcgctc cagtcaatga   16080
ccgctgttat gcggccattg tccgtcagga cattgttgga gccgaaatcc gcgtgcacga   16140
ggtgccggac ttcggggcag tcctcggccc aaagcatcag ctcatcgaga gcctgcgcga   16200
cggacgcact gacggtgtcg tccatcacag tttgccagtg atacacatgg ggatcagcaa   16260
tcgcgcatat gaaatcacgc catgtagtgt attgaccgat tccttgcggt ccgaatgggc   16320
cgaacccgct cgtctggcta agatcggccg cagcgatcgc atccatagcc tccgcgaccg   16380
gttgtagaac agcgggcagt tcggtttcag gcaggtcttg caacgtgaca ccctgtgcac   16440
ggcgggagat gcaataggtc aggctctcgc taaactcccc aatgtcaagc acttccgaaa   16500
tcgggagcgc ggccgatgca aagtgccgat aaacataacg atctttgtag aaaccatcgg   16560
cgcagctatt tacccgcagg acatatccac gccctcctac atcgaagctg aaagcacgag   16620
attcttcgcc ctccgagagc tgcatcaggt cggagacgct gtcgaacttt tcgatcagaa   16680
acttctcgac agacgtcgcg gtgagttcag gcttttttcat atctcattgc ccccggatc   16740 tgcgaaagct cgagagagat agatttgtag agagagactg gtgatttcag cgtgtcctct   16800
ccaaatgaaa tgaacttcct tatatagagg aaggtcttgc gaaggatagt gggattgtgc   16860
gtcatccctt acgtcagtgg agatatcaca tcaatccact tgcttgaag acgtggttgg   16920 aacgtcttct ttttccacga tgctcctcgt gggtgggggt ccatctttgg gaccactgtc   16980
ggcagaggca tcttgaacga tagccttttcc tttatcgcaa tgatggcatt tgtaggtgcc   17040
accttccttt tctactgtcc ttttgatgaa gtgacagata gctgggcaat ggaatccgag   17100
```

-continued

```
gaggtttccc gatattaccc tttgttgaaa agtctcaata gcccttttggt cttctgagac     17160 tgtatctttg atattcttgg agtagacgag agtgtcgtgc tccaccatgt tatcacatca     17220
atccacttgc tttgaagacg tggttggaac gtcttctttt tccacgatgc tcctcgtggg     17280
tgggggtcca tctttgggac cactgtcggc agaggcatct tgaacgatag cctttccttt     17340
atcgcaatga tggcatttgt aggtgccacc ttccttttct actgtccttt tgatgaagtg     17400
acagatagct gggcaatgga atccgaggag gtttcccgat attaccctt gttgaaaagt     17460 ctcaatagcc ctttggtctt ctgagactgt atctttgata ttcttggagt agacgagagt     17520
gtcgtgctcc accatgttgg caagctgctc tagccaatac gcaaaccgcc tctccccgcg     17580
cgttggccga ttcattaatg cagctggcac gacaggtttc ccgactggaa agcgggcagt     17640
gagcgcaacg caattaatgt gagttagctc actcattagg cacccaggc tttacacttt     17700 atgcttccgg ctcgtatgtt gtgtggaatt gtgagcggat aacaatttca cacaggaaac     17760
agctatgacc atgattac                                                   17778
```

<210> SEQ ID NO 2
<211> LENGTH: 644
<212> TYPE: PRT
<213> ORGANISM: Artificial sequence
<220> FEATURE:
<223> OTHER INFORMATION: acetolactate synthase

<400> SEQUENCE: 2

```
Met Ala Thr Thr Ala Ala Ala Ala Ala Ala Leu Ser Ala Ala
1               5                   10                  15

Thr Ala Lys Thr Gly Arg Lys Asn His Gln Arg His Val Leu Pro
                20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240
```

```
Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
        260                 265                 270

Ser Arg Arg Pro Ile Leu Tyr Val Gly Gly Cys Ser Ala Ser Gly
    275                 280                 285

Asp Glu Leu Arg Trp Phe Val Glu Leu Thr Gly Ile Pro Val Thr Thr
    290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Val Tyr

<210> SEQ ID NO 3
```

<211> LENGTH: 1935
<212> TYPE: DNA
<213> ORGANISM: Artificial sequence
<220> FEATURE:
<223> OTHER INFORMATION: acetolactate synthase

<400> SEQUENCE: 3

| | | | | | |
|---|---|---|---|---|---|
| atggctacga | ccgccgcggc | cgcggccgcc | gccctgtccg | ccgccgcgac | ggccaagacc | 60 |
| ggccgtaaga | accaccagcg | acaccacgtc | cttcccgctc | gaggccgggt | ggggcggcg | 120 |
| gcggtcaggt | gctcggcggt | gtccccggtc | accccgccgt | ccccggcgcc | gccggccacg | 180 |
| ccgctccggc | cgtggggggcc | ggccgagccc | cgcaagggcg | cggacatcct | cgtggaggcg | 240 |
| ctggagcggt | gcggcgtcag | cgacgtgttc | gcctacccgg | gcggcgcgtc | catggagatc | 300 |
| caccaggcgc | tgacgcgctc | cccggtcatc | accaaccacc | tcttccgcca | cgagcagggc | 360 |
| gaggcgttcg | cggcgtccgg | gtacgcgcgc | cgtccggcc | gcgtcggggt | ctgcgtcgcc | 420 |
| acctccggcc | ccggggcaac | caacctcgtg | tccgcgctcg | ccgacgcgct | gctcgactcc | 480 |
| gtcccgatgg | tcgccatcac | gggccaggtc | ccccgccgca | tgatcggcac | cgacgccttc | 540 |
| caggagacgc | ccatagtcga | ggtcacccgc | tccatcacca | agcacaatta | ccttgtcctt | 600 |
| gatgtggagg | acatccccg | cgtcatacag | gaagccttct | tcctcgcgtc | ctcgggccgt | 660 |
| cctggcccgg | tgctggtcga | catccccaag | gacatccagc | agcagatggc | cgtgccggtc | 720 |
| tgggacacct | cgatgaatct | accagggtac | atcgcacgcc | tgcccaagcc | acccgcgaca | 780 |
| gaattgcttg | agcaggtctt | gcgtctggtt | ggcgagtcac | ggcgcccgat | tctctatgtc | 840 |
| ggtgtggct | gctctgcatc | tggtgacgaa | ttgcgctggt | tgttgagct | gactggtatc | 900 |
| ccagttacaa | ccactctgat | gggcctcggc | aatttcccca | gtgacgaccc | gttgtccctg | 960 |
| cgcatgcttg | gatgcatgg | cacggtgtac | gcaaattatg | ccgtggataa | ggctgacctg | 1020 |
| ttgcttgcgt | ttggtgtgcg | gtttgatgat | cgtgtgacag | ggaaaattga | ggcttttgca | 1080 |
| agcagggcca | agattgtgca | cattgacatt | gatccagcag | agattggaaa | gaacaagcaa | 1140 |
| ccacatgtgt | caatttgcgc | agatgttaag | cttgctttac | agggcttgaa | tgctctgcta | 1200 |
| caacagagca | caacaaagac | aagttctgat | tttagtgcat | ggcacaatga | gttggaccag | 1260 |
| cagaagaggg | agtttcctct | ggggtacaaa | acttttggtg | aagagatccc | accgcaatat | 1320 |
| gccattcagg | tgctggatga | gctgacgaaa | ggtgaggcaa | tcatcgctac | tggtgttggg | 1380 |
| cagcaccaga | tgtgggcggc | acaatattac | acctacaagc | ggccacggca | gtggctgtct | 1440 |
| tcggctggtc | tgggcgcaat | gggatttggg | ctgcctgctg | cagctggtgc | ttctgtggct | 1500 |
| aacccaggtg | tcacagttgt | tgatattgat | ggggatggta | gcttcctcat | gaacattcag | 1560 |
| gagctggcat | tgatccgcat | tgagaacctc | cctgtgaagg | tgatggtgtt | gaacaaccaa | 1620 |
| catttgggta | tggtggtgca | atgggaggat | aggttttaca | aggcgaatag | ggcgcataca | 1680 |
| tacttgggca | acccggaatg | tgagagcgag | atatatccag | attttgtgac | tattgctaag | 1740 |
| gggttcaata | ttcctgcagt | ccgtgtaaca | aagaagagta | agtccgtgc | cgccatcaag | 1800 |
| aagatgctcg | agactccagg | gccatacttg | ttggatatca | tcgtcccgca | ccaggagcat | 1860 |
| gtgctgccta | tgatcccaag | tggggcgca | ttcaaggaca | tgatcctgga | tggtgatggc | 1920 |
| aggactgtgt | attaa | | | | | 1935 |

<210> SEQ ID NO 4
<211> LENGTH: 20
<212> TYPE: DNA
<213> ORGANISM: Artificial sequence

```
<220> FEATURE:
<223> OTHER INFORMATION: primer

<400> SEQUENCE: 4
aaggtgaggc aatcatcgct                                              20

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
ccatgccaag cacatcaaac                                              20

<210> SEQ ID NO 6
<211> LENGTH: 23
<212> TYPE: DNA
<213> ORGANISM: Artificial sequence
<220> FEATURE:
<223> OTHER INFORMATION: primer

<400> SEQUENCE: 6
tcgacaagaa gtactccatc ggc                                          23

<210> SEQ ID NO 7
<211> LENGTH: 23
<212> TYPE: DNA
<213> ORGANISM: Artificial sequence
<220> FEATURE:
<223> OTHER INFORMATION: primer

<400> SEQUENCE: 7
caagagagag ggcgatcagg ttg                                          23

<210> SEQ ID NO 8
<211> LENGTH: 22
<212> TYPE: DNA
<213> ORGANISM: Artificial sequence
<220> FEATURE:
<223> OTHER INFORMATION: primer

<400> SEQUENCE: 8
gtaattcatc caggtctcca ag                                           22

<210> SEQ ID NO 9
<211> LENGTH: 18
<212> TYPE: DNA
<213> ORGANISM: Artificial sequence
<220> FEATURE:
<223> OTHER INFORMATION: primer

<400> SEQUENCE: 9
acggagaaat ttcaatgc                                                18

<210> SEQ ID NO 10
<211> LENGTH: 25
<212> TYPE: DNA
<213> ORGANISM: Artificial sequence
<220> FEATURE:
<223> OTHER INFORMATION: primer

<400> SEQUENCE: 10
ggagaacaca tgcacactaa aaaga                                        25
```

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
ttgggtaacg ccagggtttt                                          20

<210> SEQ ID NO 12
<211> LENGTH: 20
<212> TYPE: DNA
<213> ORGANISM: Artificial sequence
<220> FEATURE:
<223> OTHER INFORMATION: primer

<400> SEQUENCE: 12
gaacgcgatg ctggaagaac                                          20

<210> SEQ ID NO 13
<211> LENGTH: 20
<212> TYPE: DNA
<213> ORGANISM: Artificial sequence
<220> FEATURE:
<223> OTHER INFORMATION: primer

<400> SEQUENCE: 13
ctgttggcgt cgtagaacct                                          20

<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
gtacgagggg agtagtagtc agt                                      23

<210> SEQ ID NO 15
<211> LENGTH: 20
<212> TYPE: DNA
<213> ORGANISM: Artificial sequence
<220> FEATURE:
<223> OTHER INFORMATION: primer

<400> SEQUENCE: 15
tgaggttgag cttgtggagc                                          20

<210> SEQ ID NO 16
<211> LENGTH: 21
<212> TYPE: DNA
<213> ORGANISM: Artificial sequence
<220> FEATURE:
<223> OTHER INFORMATION: primer

<400> SEQUENCE: 16 tttctcccctt gttcgcatct g                                       21

<210> SEQ ID NO 17
<211> LENGTH: 20
<212> TYPE: DNA
<213> ORGANISM: Artificial sequence
<220> FEATURE:
<223> OTHER INFORMATION: primer

<400> SEQUENCE: 17
ggcagcttaa tcatgggcag                                               20

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
aaccgcatgc tcgagaagat                                               20

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
ttgtgcacgg tacaccactt                                               20

<210> SEQ ID NO 20
<211> LENGTH: 18
<212> TYPE: DNA
<213> ORGANISM: Artificial sequence
<220> FEATURE:
<223> OTHER INFORMATION: primer

<400> SEQUENCE: 20
gcacacctgg ctccaacc                                                 18

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
tcggcaaacc aagagaacga                                               20

<210> SEQ ID NO 22
<211> LENGTH: 23
<212> TYPE: DNA
<213> ORGANISM: Artificial sequence
<220> FEATURE:
<223> OTHER INFORMATION: chr04:19170867-19170889 of Oryza sativa
     Nipponbare

<400> SEQUENCE: 22
gggcatggtg gtgcagtggg agg                                           23

<210> SEQ ID NO 23
<211> LENGTH: 23
<212> TYPE: DNA
<213> ORGANISM: Artificial sequence
<220> FEATURE:
<223> OTHER INFORMATION: chr03:1562250-1562272 of Oryza sativa
     Nipponbare

<400> SEQUENCE: 23
gggtgtggtg ctgcattggg tgg                                           23

<210> SEQ ID NO 24
<211> LENGTH: 22
<212> TYPE: DNA
<213> ORGANISM: Artificial sequence
<220> FEATURE:
<223> OTHER INFORMATION: chr09:15887010-15887031 of Oryza sativa
      Nipponbare

<400> SEQUENCE: 24
ggccaccact ggggatcatt gg                                              22

<210> SEQ ID NO 25
<211> LENGTH: 23
<212> TYPE: DNA
<213> ORGANISM: Artificial sequence
<220> FEATURE:
<223> OTHER INFORMATION: chr01:36565231-36565253 of Oryza sativa
      Nipponbare

<400> SEQUENCE: 25
ccggtgctcc caggtgggag cgc                                             23

<210> SEQ ID NO 26
<211> LENGTH: 23
<212> TYPE: DNA
<213> ORGANISM: Artificial sequence
<220> FEATURE:
<223> OTHER INFORMATION: chr10:17913749-17913771 of Oryza sativa
      Nipponbare

<400> SEQUENCE: 26
gagcccccac gtgggagcaa cgg                                             23

<210> SEQ ID NO 27
<211> LENGTH: 26
<212> TYPE: DNA
<213> ORGANISM: Artificial sequence
<220> FEATURE:
<223> OTHER INFORMATION: ALS gene of Oryza sativa Nipponbare

<400> SEQUENCE: 27
tttgggtatg gtggtgcaat gggagg                                          26

<210> SEQ ID NO 28
<211> LENGTH: 26
<212> TYPE: DNA
<213> ORGANISM: Artificial sequence
<220> FEATURE:
<223> OTHER INFORMATION: modified ALS gene of Oryza sativa Nipponbare

<400> SEQUENCE: 28
tttgggtatg gtcgtccagt tggagg                                          26

<210> SEQ ID NO 29
<211> LENGTH: 28
<212> TYPE: DNA
<213> ORGANISM: Artificial sequence
<220> FEATURE:
<223> OTHER INFORMATION: ALS gene of Oryza sativa Nipponbare

<400> SEQUENCE: 29
cctatgatcc caagtggggg cgcattca                                        28

<210> SEQ ID NO 30
<211> LENGTH: 28
<212> TYPE: DNA

<213> ORGANISM: Artificial sequence
<220> FEATURE:
<223> OTHER INFORMATION: modified ALS gene of Oryza sativa Nipponbare

<400> SEQUENCE: 30
cctatgatcc caattggcgg ggcgttta                                28

<210> SEQ ID NO 31
<211> LENGTH: 28
<212> TYPE: DNA
<213> ORGANISM: Artificial sequence
<220> FEATURE:
<223> OTHER INFORMATION: ALS gene of Oryza sativa Nipponbare

<400> SEQUENCE: 31
cctatgatcc caagtggggg cgcattca                                28

<210> SEQ ID NO 32
<211> LENGTH: 28
<212> TYPE: DNA
<213> ORGANISM: Artificial sequence
<220> FEATURE:
<223> OTHER INFORMATION: modified ALS gene of Oryza sativa Nipponbare

<400> SEQUENCE: 32
cctatgatcc caattggcgg ggcgttca                                28

<210> SEQ ID NO 33
<211> LENGTH: 28
<212> TYPE: DNA
<213> ORGANISM: Artificial sequence
<220> FEATURE:
<223> OTHER INFORMATION: ALS gene of Oryza sativa Nipponbare

<400> SEQUENCE: 33
cctatgatcc caagtggggg cgcattca                                28

<210> SEQ ID NO 34
<211> LENGTH: 28
<212> TYPE: DNA
<213> ORGANISM: Artificial sequence
<220> FEATURE:
<223> OTHER INFORMATION: modified ALS gene of Oryza sativa Nipponbare

<400> SEQUENCE: 34
cctatgatcc caattggcgg ggcattca                                28

<210> SEQ ID NO 35
<211> LENGTH: 271
<212> TYPE: DNA
<213> ORGANISM: Artificial sequence
<220> FEATURE:
<223> OTHER INFORMATION: ALS gene of Oryza sativa Nipponbare

<400> SEQUENCE: 35
gggtatggtg gtgcaatggg aggataggtt ttacaaggcg aatagggcgc atacatactt    60
gggcaacccg gaatgtgaga gcgagatata tccagatttt gtgactattg ctaaggggtt   120
caatattcct gcagtccgtg taacaaagaa gagtgaagtc cgtgccgcca tcaagaagat   180
gctcgagact ccagggccat acttgttgga tatcatcgtc ccgcaccagg agcatgtgct   240
gcctatgatc caagtggggg cgcattcaa g                                   271

<210> SEQ ID NO 36
<211> LENGTH: 271

```
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 36
gggtatggtc gtccagttgg aggataggtt ttacaaggcg aatagggcgc atacatactt      60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga catcatcgtc ccgcaccagg agcatgtgct    240
gcctatgatc ccaattggcg gggcgtttaa g                                   271

<210> SEQ ID NO 37
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 37
gggtatggtc gtccagttgg aggataggtt ttacaaggcg aatagggcgc atacatactt      60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga catcatcgtc ccgcaccagg agcatgtgct    240
gcctatgatc ccaattggcg gggcattcaa g                                   271

<210> SEQ ID NO 38
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 38
gggtatggtc gtccagttgg aggataggtt ttacaaggcg aatagggcgc atacatactt      60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga catcatcgtc ccgcaccagg agcatgtgct    240
gcctatgatc ccaattggcg gggcgtttaa g                                   271

<210> SEQ ID NO 39
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 39
gggtatggtc gtccagttgg aggataggtt ttacaaggcg aatagggcgc atacatactt      60
gggcaacccg gaatgtgaga gcgagatata tccagatttt gtgactattg ctaaggggtt    120
```
caatattcct gcagtccgtg taacaaagaa gagtgaagtc cgtgccgcca tcaagaagat    180
gctcgagact ccagggccat acttgttgga catcatcgtc ccgcaccagg agcatgtgct    240
gcctatgatc ccaattggcg gggcgttcaa g                                    271

<210> SEQ ID NO 40
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 40
gggtatggtc gtccagttgg aggataggtt ttacaaggcg aatagggcgc atacatactt     60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga catcatcgtc ccgcaccagg agcatgtgct    240
gcctatgatc ccaattggcg gggcattcaa g                                    271

<210> SEQ ID NO 41
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 41
gggtatggtc gtccagttgg aggataggtt ttacaaggcg aatagggcgc atacatactt     60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga tatcatcgtc ccgcaccagg agcatgtgct    240
gcctatgatc ccaagtgggg gcgcattcaa g                                    271

<210> SEQ ID NO 42
<211> LENGTH: 271
<212> TYPE: DNA
<213> ORGANISM: Artificial sequence
<220> FEATURE:
<223> OTHER INFORMATION: ALS gene of Oryza sativa Nipponbare

<400> SEQUENCE: 42
gggtatggtg gtgcaatggg aggataggtt ttacaaggcg aatagggcgc atacatactt     60
gggcaacccg gaatgtgaga gcgagatata tccagatttt gtgactattg ctaaggggtt    120
caatattcct gcagtccgtg taacaaagaa gagtgaagtc cgtgccgcca tcaagaagat    180
gctcgagact ccagggccat acttgttgga tatcatcgtc ccgcaccagg agcatgtgct    240
gcctatgatc ccaagtgggg gcgcattcaa g                                    271

<210> SEQ ID NO 43
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 43

```
gggtatggtc gtccagttgg aggataggtt ttacaaggcg aatagggcgc atacatactt      60
gggcaacccg gaatgtgaga gcgagatata tccagatttt gtgactattg ctaaggggtt     120
caatattcct gcagtccgtg taacaaagaa gagtgaagtc cgtgccgcca tcaagaagat     180
gctcgagact ccagggccat acttgttgga catcatcgtc ccgcaccagg agcatgtgct     240
gcctatgatc ccaattggcg gggcgtttaa g                                    271
```

<210> SEQ ID NO 44
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group of Oryza sativa Nipponbare

<400> SEQUENCE: 44

```
gggtatggtc gtccagttgg aggataggtt ttacaaggcg aatagggcgc atacatactt      60
gggcaacccg gaatgtgaga gcgagatata tccagatttt gtgactattg ctaaggggtt     120
caatattcct gcagtccgtg taacaaagaa gagtgaagtc cgtgccgcca tcaagaagat     180
gctcgagact ccagggccat acttgttgga tatcatcgtc ccgcaccagg agcatgtgct     240
gcctatgatc ccaagtgggg gcgcattcaa g                                    271
```

<210> SEQ ID NO 45
<211> LENGTH: 271
<212> TYPE: DNA
<213> ORGANISM: Artificial sequence
<220> FEATURE:
<223> OTHER INFORMATION: mutation results of the nucleotide sequences
      adjacent to the 548th amino acid and the 627th amino acid of ALS
      of the plants in Cas9-arm donor group  of Oryza sativa Nipponbare

<400> SEQUENCE: 45

```
gggtatggtg gtgcaattgg gaggagcaca tgctcctggt gcgggacgat gatatccaac      60
aagtatggcc ctggagtctc gagcatcttc ttgatggcgg cacggacttc actcttcttt     120
gttacacgga ctgcaggaat attgaacccc ttagcaatag tcacaaaatc tggatatatc     180
tcgctctcac attccgggtt gcccaagtat gtatgcgccc tattcgcctt gtaaaacctg     240
cctatgaatc ccaaggggggg gcgcattcaa g                                   271
```

What is claimed:

1. A composition for site-specific modification in a plant genome, comprising a vector for site-specific modification in the plant genome and a donor DNA A;
   wherein the vector for site-specific modification in the plant genome comprises a Cas9 protein expression cassette, a gRNA expression cassette, and a donor DNA B;
   wherein the gRNA expression cassette encodes two gRNAs targeting two target sites in a target DNA of a plant of interest;
   wherein the target DNA of the plant of interest comprises a fragment to be site-specifically modified which is positioned between the two target sites in the target DNA of the plant of interest;
   wherein of the two target sites, one positioned upstream is an upstream target site,
   wherein the other one positioned downstream is a downstream target site;
   wherein the donor DNA B comprises the upstream target site, the downstream target site, and a fragment for site-specific modification positioned between the upstream target site and the downstream target site;
   wherein the fragment for site-specific modification is a DNA fragment to replace the fragment to be site-specifically modified in the target DNA;
   wherein the donor DNA A is other than the vector and has a same nucleotide sequence as the donor DNA B, and
   wherein: the upstream target site consists of nucleotides at positions 7590-7609 from 5'-end of SEQ ID NO: 1; the downstream target site consists of nucleotides at positions 8032-8051 from 5'-end of SEQ ID NO: 1; the fragment for site-specific modification is set forth by the nucleotides at positions 7716-7979 from 5'-end of SEQ ID NO: 1.

2. The composition according to claim 1, wherein: the plant of interest is a monocotyledonous plant or a dicotyledonous plant.

3. The composition according to claim 2, wherein: the monocotyledonous plant is a gramineous plant.

4. The composition according to claim 1, wherein: the target DNA is a gene encoding acetolactate synthase.

5. The composition according to claim 4, wherein: the acetolactate synthase is a protein with the amino acid sequence as set forth by SEQ ID NO: 2.

6. The composition according to claim 5, wherein: the target DNA is SEQ ID NO: 3.

7. The composition according to claim 4, wherein: the gRNA expression cassette includes a gRNA expression cassette 1 encoding gRNA1, and a gRNA expression cassette 2 encoding gRNA2, wherein the gRNA1 targets the upstream target site, and the gRNA2 targets the downstream target site.

8. The composition according to claim 7, wherein: the gRNA expression cassette 1 is nucleotides at positions 261-747 from 5'-end of SEQ ID NO: 1; and the gRNA expression cassette 2 is nucleotides at positions 8328-8814 from 5'-end of SEQ ID NO: 1.

9. The composition according to claim 8, wherein:
the vector for the site-specific modification in the plant genome is SEQ ID NO: 1; and
the donor DNA A is nucleotides at positions 7590-8051 from 5'-end of SEQ ID NO: 1.

10. A method for site-specific modification in a plant genome, comprising:
introducing into a plant of interest a vector for site-specific modification in the plant genome and a donor DNA A to obtain a plant with the plant genome site-specifically modified;
wherein the vector for site-specific modification in the plant genome comprises a Cas9 protein expression cassette, gRNA expression cassettes, and a donor DNA B;
wherein the gRNA expression cassettes encode two gRNAs targeting two target sites in a target DNA of a plant of interest, respectively;
wherein the target DNA of the plant of interest comprises a fragment to be site-specifically modified positioned between the two target sites in the target DNA of the plant of interest;
wherein a first of the two target sites is an upstream target site;
wherein a second of the two target sites is a downstream target site;
wherein the donor DNA B comprises the upstream target site, the downstream target site, and a fragment for site-specific modification positioned between the upstream target site and the downstream target site;
wherein the fragment for site-specific modification is a DNA fragment to replace the fragment to be site-specifically modified in the target DNA; and
wherein the donor DNA A has a same nucleotide sequence as the donor DNA B,
wherein: the upstream target site consists of nucleotides at positions 7590-7609 from 5'-end of SEQ ID NO: 1; the downstream target site consists of nucleotides at positions 8032-8051 from 5'-end of SEQ ID NO: 1; and the fragment for site-specific modification is set forth by the nucleotides at positions 7716-7979 from 5'-end of SEQ ID NO: 1.

11. The method according to claim 10, wherein: the vector for site-specific modification in the plant genome and the donor DNA A is introduced into the plant of interest in a molar ratio of 1:(1-40).

12. A method for producing herbicide-resistance in a plant, comprising:
introducing into a plant of interest a vector for site-specific modification in the plant genome and a donor DNA A to obtain a plant with the plant genome site-specifically modified;
wherein the vector for site-specific modification in the plant genome comprises a Cas9 protein expression cassette, a gRNA expression cassette, and a donor DNA B;
wherein the gRNA expression cassette encodes two gRNAs targeting two target sites in a target DNA of a plant of interest, respectively;
wherein the target DNA of the plant of interest comprises a fragment to be site-specifically modified positioned between the two target sites in the target DNA of the plant of interest;
wherein a first of the two target sites is an upstream target site;
wherein a second of the two target sites is a downstream target site;
wherein the donor DNA B comprises the upstream target site, the downstream target site, and a fragment for site-specific modification positioned between the upstream target site and the downstream target site;
wherein the fragment for site-specific modification is a DNA fragment to replace the fragment to be site-specifically modified in the target DNA; and
wherein the donor DNA A has a same nucleotide sequence as the donor DNA B,
wherein: the upstream target site consists of nucleotides at positions 7590-7609 from 5'-end of SEQ ID NO: 1; the downstream target site consists of nucleotides at positions 8032-8051 from 5'-end of SEQ ID NO: 1; and the fragment for site-specific modification is set forth by the nucleotides at positions 7716-7979 from 5'-end of SEQ ID NO: 1.

13. The method according to claim 12, wherein the target DNA is a gene encoding acetolactate synthase.

14. The method according to claim 12, wherein the plant of interest is a monocotyledonous plant or a dicotyledonous plant.

* * * * *